(12) United States Patent
Kermani et al.

(10) Patent No.: US 8,407,554 B2
(45) Date of Patent: Mar. 26, 2013

(54) METHOD AND APPARATUS FOR QUANTIFICATION OF DNA SEQUENCING QUALITY AND CONSTRUCTION OF A CHARACTERIZABLE MODEL SYSTEM USING REED-SOLOMON CODES

(75) Inventors: Bahram Ghaffarzadeh Kermani, Los Altos, CA (US); Karen W. Shannon, Encinitas, CA (US)

(73) Assignee: Complete Genomics, Inc., Mountain View, CA (US)

( * ) Notice: Subject to any disclaimer, the term of this patent is extended or adjusted under 35 U.S.C. 154(b) by 489 days.

(21) Appl. No.: 12/697,995

(22) Filed: Feb. 1, 2010

(65) Prior Publication Data

US 2010/0199155 A1 Aug. 5, 2010

Related U.S. Application Data

(60) Provisional application No. 61/149,617, filed on Feb. 3, 2009.

(51) Int. Cl.
*H03M 13/03* (2006.01)
*H03M 13/15* (2006.01)
(52) U.S. Cl. ........................... 714/752; 714/784
(58) Field of Classification Search .......... 714/755, 714/784, 752
See application file for complete search history.

(56) References Cited

U.S. PATENT DOCUMENTS

| 4,584,686 | A | 4/1986 | Fritze |
| 6,430,723 | B2 | 8/2002 | Kodama et al. |
| 7,228,485 | B1 | 6/2007 | Wu et al. |
| 2005/0089860 | A1* | 4/2005 | Arita ............................. 435/6 |
| 2007/0042372 | A1* | 2/2007 | Arita ............................. 435/6 |
| 2007/0113137 | A1 | 5/2007 | Ryu |
| 2008/0320358 | A1 | 12/2008 | Pandel et al. |
| 2009/0172501 | A1 | 7/2009 | Lablans |
| 2010/0192032 | A1* | 7/2010 | Chen et al. ................. 714/746 |

OTHER PUBLICATIONS

International Search Report and Written Opinion corresponding to the PCT application No. PCT/US2010/023083, date of mailing Mar. 30, 2010, 8 pages total.
Drmanac et al., "Human Genome Sequencing Using Unchained Base Reads on Self-Assembling DNA Nanoarrays", pp. 78-81, Science, Jan. 1, 2010, vol. 327. No. 5961, Originally published in Science Express on Nov. 5, 2009.
Sklar, B., "Reed-Solomon Codes," Apr. 12, 2002, 33 pages, retrieved from the internet <URL: hscc.cs.nthu.edu.tw/~sheujp/lecture_note/rs.pdf>.
Hamady, M, et al., "Error-correcting barcoded primers allow hundreds of samples to be pyrosequenced in multiplex," NIH Public Access Author Manuscript, 6 pages, published in final edited form as: Nat Methods, Mar. 2008, vol. 5(3), pp. 235-237.
Sylvester, J., "Reed Solomon Codes," Jan. 2001, 7 pages, retrieved from the internet <URL:www.csupomona.edu/~jskang/files/rs1.pdf>.

(Continued)

*Primary Examiner* — Stephen M Baker
(74) *Attorney, Agent, or Firm* — Kilpatrick Townsend & Stockton LLP

(57) ABSTRACT

Data extracted from fluorosphore responses of fluorophore labeled bases in genetic material used in sequencing of unknown fragments from a defined set of for example a model system are converted into a class of block codes that are then employed in a computer-based process to compare and correct preliminary calls of calls of the categorically known genetic material. In a specific embodiment, the Reed-Solomon codes are employed to identify one or more errors as may occur in a finite block of codes. The methodology is also useful to identify elements of a real system containing known elements in the form of a tag. Reed-Solomon sensors may be employed with and in addition to other types of genome sensors.

62 Claims, 3 Drawing Sheets

OTHER PUBLICATIONS

Bonaldo, M. F., et al., "Normalization and subtraction: two approaches to facilitate gene discovery," Genome Research, 1996, vol. 6, pp. 791-806.

Frank, D. N., "Barcrawl and Bartab: software tools for the design and implementation of barcoded primers for highly multiplexed DNA sequencing," BMC Bioinformatics 2009, [online], Oct. 29, 2009, 13 pages, retrieved from the internet <URL: http://www.biomedcentral.com/1471-2105/10/362>.

Meyer, M., et al., "Targeted high-throughput sequencing of tagged nucleic acid samples," Nucleic Acids Research, 2007, vol. 35, No. 15, 5 pages.

Parameswaran, P., et al., "A pyrosequencing-tailored nucleotide barcode design unveils opportunities for large-scale sample multiplexing," Nucleic Acids Research, 2007, vol. 35, No. 19, 9 pages.

* cited by examiner

| Index | Observed Sequence | Corrected Sequence | Solomon Recovered | Score 1 | Score 2 | Score 3 | Score 4 | Score 5 | Score 6 | Score 7 |
|---|---|---|---|---|---|---|---|---|---|---|
| 2560 | TACGTAG | TACGTAG | 0 | 0.84 | 0.82 | 0.81 | 0.32 | 0.81 | 0.84 | 0.09 |
| 2561 | TGGCTAA | TGGCAAA | 1 | 0.06 | 0.01 | 0.01 | 0 | 0.01 | 0.1 | 0.05 |
| 2562 | TGGCAAA | TGGCAAA | 0 | 0.94 | 0.86 | 0.87 | 0.87 | 0.85 | 0.9 | 0.95 |
| 2563 | AGGAAAA | AGGAAAG | 1 | 0 | 0.05 | 0.04 | 0 | 0 | 0.01 | 0 |
| 2564 | AGGAAAG | AGGAAAG | 0 | 0.13 | 0.21 | 0.28 | 0.12 | 0.21 | 0.05 | 0.12 |

| Categories | Observed Sequences | Reed-Solomon Corrected Sequences |
|---|---|---|
| Number of Valid Sequences | 20647 | 35317 |
| Number of UnCalled Sequences | 0 | 15308 |
| Number of Invalid Sequences | 29978 | 0 |
| Total | 50625 | 50625 |

| Index | Observed Sequence | Corrected Sequence | Reed-Solomon Recovered | Score 1 | Score 2 | Score 3 | Score 4 | Score 5 | Score 6 | Score 7 | Score 8 | Score 9 | Score 10 |
|---|---|---|---|---|---|---|---|---|---|---|---|---|---|
| 20 | CGGTTCTTAT | CGGTACTTAT | 1 | 0.1574 | 0.4825 | 0.2193 | 0.4314 | 0.0104 | 0.2906 | 0.2856 | 0.0262 | 0.0254 | 0.1353 |
| 29 | GTAAGACTGC | GTAAGACTGC | 0 | 0.9143 | 0.8828 | 0.9396 | 0.9122 | 0.8947 | 0.9499 | 0.959 | 0.9488 | 0.9444 | 0.9335 |
| 30 | AGACTGGCGC | AGACTGGAGC | 1 | 0.0968 | 0.0579 | 0.114 | 0.0141 | 0.0735 | 0.2902 | 0.3316 | 0.0029 | 0.4844 | 0.5554 |
| 37 | AGGACACCGC | AGGATACCGC | 1 | 0.9943 | 0.0615 | 0.5716 | 0.6492 | 0.0587 | 0.1396 | 0.1302 | 0.1057 | 0.1038 | 0.9983 |
| 40 | CGCGAGTCGA | CGCGAGTCGA | 0 | 0.1824 | 0.886 | 0.9227 | 0.911 | 0.9232 | 0.9505 | 0.9399 | 0.97 | 0.9421 | 0.9668 |
| 50 | AAAAGTCCGG | AAAAGTCCGG | 0 | 0.8932 | 0.8876 | 0.8989 | 0.8734 | 0.8854 | 0.2525 | 0.6954 | 0.8807 | 0.9075 | 0.9415 |
| 68 | ACTTTATTAC | ********** | 0 | 0 | 0.0007 | 0.0406 | 0 | 0 | 0 | 0 | 0 | 0 | 0 |
| 69 | ACTAACCGTA | ACTAACCGTA | 0 | 0.8452 | 0.8646 | 0.8521 | 0.8821 | 0.6185 | 0.8762 | 0.882 | 0.8881 | 0.8917 | 0.882 |
| 70 | CACATGTTAC | CACATGTTAC | 0 | 0.9579 | 0.9647 | 0.981 | 0.974 | 0.9926 | 0.9801 | 0.9575 | 0.9429 | 0.9281 | 0.9401 |
| 71 | TTGCGGGCTT | TTGCGGGCCT | 1 | 0.4263 | 0.6358 | 0.3367 | 0.1561 | 0.4507 | 0.2606 | 0.2678 | 0.2049 | 0.0075 | 0.5003 |
| 73 | TACTCAGTCA | CACTCAGTCA | 1 | 0 | 0.3616 | 0.3828 | 0.6239 | 0.174 | 0.2373 | 0.0189 | 0.3441 | 0.0502 | 0.0959 |
| 74 | CTAGAGTTTC | CTAGAGTTTC | 0 | 0.3268 | 0.9163 | 0.9362 | 0.9205 | 0.9314 | 0.9724 | 0.9342 | 0.9254 | 0.9255 | 0.9675 |
| 85 | ACACCACCGC | ACACCACCGC | 0 | 0.7051 | 0.9319 | 0.903 | 0.9003 | 0.8817 | 0.9548 | 0.9731 | 0.9805 | 0.9563 | 0.9484 |
| 109 | ACACAACGCC | ACACGACGCC | 1 | 0.7707 | 0.0847 | 0.8321 | 0.0349 | 0.0093 | 0.9404 | 0.9251 | 0.9244 | 0.9463 | 0.9096 |

*FIG. 4*

METHOD AND APPARATUS FOR QUANTIFICATION OF DNA SEQUENCING QUALITY AND CONSTRUCTION OF A CHARACTERIZABLE MODEL SYSTEM USING REED-SOLOMON CODES

CROSS-REFERENCES TO RELATED APPLICATIONS

The present application claims benefit under 35 USC 119 (e) of U.S. provisional Application No. 61/149,617, filed on Feb. 3, 2009, entitled "Method And Apparatus For Correcting DNA Sequencing Errors Using Reed-Solomon Codes," the content of which is incorporated herein by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The invention relates to techniques for characterizing the accuracy of genome sequence analysis, and more particularly to the use of advanced mathematical methods for correction of observational errors in sequences having portions of known content.

Large-scale genomic sequence analysis ("sequencing") is a key step toward understanding a wide range of biological phenomena. The need for low-cost, high-throughput sequencing and re-sequencing has led to the development of new approaches to sequencing that employ parallel analysis of multiple nucleic acid targets simultaneously.

Conventional methods of sequencing are generally restricted to determining a few tens of nucleotides before signals become significantly degraded, thus placing a significant limit on overall sequencing efficiency. Conventional methods of sequencing are also often limited by signal-to-noise ratios that render such methods unsuitable for single-molecule sequencing.

A challenge of genome sequencing is the accurate recognition, identification, characterization and classification of DNA strands. Efforts have been developed for improving DNA sensing, analysis and measurement throughput by manipulation of DNA including the manipulation of DNA nanoballs ("DNB"). The techniques for sequencing DNB involve the categorization of fluorophore responses of DNB at genome attachment sites on rigid substrates in the presence of interference from adjacent attachment sites. A specific categorization is known as a call, as hereinafter explained. Signal-to-noise ratios in DNA sequencing can be relatively low, which adversely impacts base quality score.

Improvements in base quality score would allow better characterization of the sequencing system and its failure modes. Improvements would also allow one to quantify improvements in such aspects as the substrate, the biochemistry, the methodology of preparation of samples, the mechanical systems and optical systems, and the mathematical algorithms that analyze and yield the calls.

Linear block cyclic symbol-based error correction methods relying on error correcting codes have been used to identify and correct bit streams in impaired communication channels, subject to limitations on error rate and run length. Types of codes used in the past for error correction of bit errors in DNA are the Hamming codes. These codes are capable of correcting for one bit error but not one base error. However, Hamming codes are not capable of correcting a large number of errors in a sequence.

Reed-Solomon error detection/correction is a method based on an error-correcting code that works by oversampling a polynomial constructed from the data. Sampling the polynomial more often than is necessary makes the polynomial over-determined. As long as more than a minimum number of the samples are correct, the original polynomial can be recovered in the presence of a some bad points. The relationship between to good and bad points determines the number of errors that can be corrected.

Reed-Solomon codes have been explained at length in the mathematics and communication literature. See for example *Error Control Coding: Fundamentals and Applications* by Shu Lin and Daniel Costello; Prentice Hall; and *Error Control Systems for Digital Communication and Storage*, by Stephen B. Wicker; Prentice Hall. It has been shown that if it is guaranteed that there are less than one error in a string of seven values in a sequence having four possible values, then the related mathematics can guarantee that an error in the seven-member long sequence can be captured and corrected.

It would be advantageous for the field of genome analysis if methods could be designed to characterize and potentially increase the accuracy and call-rate/efficiency of sequencing.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The practice of genome analysis may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. The present invention focuses on the detection problem. Conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press); Stryer, L. (1995) *Biochemistry* (4th Ed.) Freeman, New York, Gait, "*Oligonucleotide Synthesis: A Practical Approach,*" 1984, IRL Press, London, Nelson and Cox (2000); Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following definitions may be helpful in providing background for an understanding of the invention.

"Adaptor" refers to an engineered construct comprising "adaptor elements" where one or more adaptors may be interspersed within target nucleic acid in a library construct. The adaptor elements or features included in any adaptor vary widely depending on the use of the adaptors, but typically include sites for restriction endonuclease recognition and/or cutting, sites for primer binding (for amplifying the library constructs) or anchor primer binding (for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as at least one and typically two "arms"; 3) different and distinct anchor binding sites at the 5' and/or the 3' ends of the adaptor for use in sequencing of adjacent target nucleic acid; and 4) optionally one or more restriction sites "Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependant amplification and like reactions (see, e.g., U.S. Pat. Nos. 4,683,195; 4,965,188; 4,683,202; 4,800159; 5,210,015; 6,174,670; 5,399,491; 6,287,824 and 5,854,033; and US Pub. No. 2006/0024711).

"Circle dependant replication" or "CDR" refers to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, concatamer of multiple copies of a strand of the template.

"Circle dependant amplification" or "CDA" refers to multiple displacement amplification of a double-stranded circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatameric double-stranded fragments.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. (Univeral bases may be used in some appropriate in some applications.) Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly- or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick base pairing.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the Tm for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5× SSPE (750 mM NaCl, 50 mM sodium phosphate, 5 mM EDTA at pH 7.4) and a temperature of 30° C. are suitable for allele-specific probe hybridizations.

"Isolated" means substantially separated or purified away from contaminants by standard methods. In the case of biological heteropolymers such as polynucleotides (DNA, RNA, etc.) for example, the polynucleotide is substantially separated or purified away from other polynucleotides and other contaminants that are present in the cell of the organism in which the polynucleotide naturally occurs. The term "isolated" also means chemically synthesized or, in the case of a polynucleotide or polypeptide, produced by recombinant expression in a host cell.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Microarray" or "array" refers to a solid phase support having a surface, preferably but not exclusively a planar or substantially planar surface, which carries an array of sites containing nucleic acids such that each site of the array comprises identical copies of oligonucleotides or polynucleotides and is spatially defined and not substantially overlapping with other member sites of the array; that is, the sites are spatially discrete. The array or microarray can also comprise a non-planar structure with a surface such as a bead or a well. The oligonucleotides or polynucleotides of the array may be covalently bound to the solid support, or may be non-covalently bound. Conventional microarray technology is reviewed in, e.g., Schena, Ed. (2000), Microarrays: A Practical Approach (IRL Press, Oxford). As used herein, "random array" or "random microarray" refers to a microarray where the identity of the oligonucleotides or polynucleotides is not discernable, at least initially, from their location but may be determined by a particular operation on the array, such as by sequencing, hybridizing decoding probes or the like. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Nucleic acid", "oligonucleotide", "polynucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Preselected," when used in reference to a block of a monomer subunit sequence that has a coding corresponding to at least one Reed-Solomon code, means that the heteropolymer is designed and/or synthesized to include the block of monomer sequence or that the block of monomer sequence is added to a preexisting heteropolymer sequence. For example, by way of illustration, a polynucleotide can be designed to include a block of five to ten nucleotide bases, such as the seven or ten nucleotide base sequences described herein, or a polynucleotide containing such a five to ten base block can be added to a preexisting polynucleotide by ligation or other standard methods.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Probes used in certain aspects of the claimed invention are labeled in a way that permits detection, e.g., with a fluorescent or other optically-discernable tag.

"Sequence determination" in reference to a target nucleic acid means determination of information relating to the sequence of nucleotides in the target nucleic acid. Such information may include the identification or determination of partial as well as full sequence information of the target nucleic acid. The sequence information may be determined with varying degrees of statistical reliability or confidence. In one aspect, the term includes the determination of the identity and ordering of a plurality of contiguous nucleotides in a target nucleic acid starting from different nucleotides in the target nucleic acid.

"Substrate" refers to a solid phase support having a surface, usually planar or substantially planar, which carries an array of sites for attachment of nucleic acid macromolecules such that each site of the array is spatially defined and not overlapping with other member sites of the array; that is, the sites are spatially discrete and optically resolvable. The nucleic acid macromolecules of the substrates of the invention may be covalently bound to the solid support, or may be non-covalently bound, i.e. through electrostatic forces. Conventional microarray technology is reviewed in, e.g., Schena, Ed. (2000), Microarrays: A Practical Approach (IRL Press, Oxford).

"Macromolecule" used in relation to a nucleic acid means a nucleic acid having a measurable three dimensional structure, including linear nucleic acid molecules with comprising secondary structures (e.g., amplicons), branched nucleic acid molecules, and multiple separate copies of individual with interacting structural elements, e.g., complementary sequences, palindromes, or other sequence inserts that cause three-dimensional structural elements in the nucleic acid.

"Target nucleic acid" means a nucleic acid from a gene, a regulatory element, genomic DNA, cDNA, RNAs including mRNAs, rRNAs, siRNAs, miRNAs and the like and fragments thereof. A target nucleic acid may be a nucleic acid from a sample, or a secondary nucleic acid such as a product of an amplification reaction.

Although the present invention is described primarily with reference to specific embodiments, it is also envisioned that other embodiments will become apparent to those skilled in the art upon reading the present disclosure, and it is intended that such embodiments be contained within the present inventive methods.

SUMMARY OF THE INVENTION

According to the invention, data extracted from labeled bases in genetic material, such as fluorosphore responses of fluorophore labeled bases in genetic material, used in sequencing of unknown fragments from a defined set of for example a model system are converted into a class of block codes that are then employed in a computer-based process to compare and correct preliminary calls of the unknown genetic material. In a specific embodiment, the Reed-Solomon codes are employed to identify, detect and preferably correct one or more errors as may occur in a finite block of codes corresponding to a DNA sequence. The methodology is not only useful for verification of known sequences of a model system used to characterize a real system, it is useful to identify elements of a real system containing known elements in the form of a tag. Reed-Solomon sensors may be employed with and in addition to other types of genome sensors. Compositions of materials are disclosed that can serve as models and diagnostic tools.

In a specific embodiment of the invention, using a seven base model system and more specifically an RS(7,5) code using 256 (7-base) sequences, namely having a block size of seven and information content of five, Reed-Solomon error correction can unambiguously correct one short burst of error, i.e., a single base transition error in a sequence, as well as correct two no-calls. (A no-call is: 1) a base that could not be called; or 2) a base that has a quality score less than a preselected confidence threshold.) As a consequence, processing according to the invention can recover 100% of the valid DNB call sequences that incurred 1 error or less in their 7-base sequence while suppressing many invalid or low quality DNB call sequences.

A further specific embodiment and in some applications a preferred embodiment comprises a 10-base model system, namely, an RS(10,8) code using 4096 (10-base) sequences that is capable of greater error correction. It is also to be understood that a 5-base model system may also be usefully employed under selected conditions, namely an RS(5,3) code using 5-base sequences.

Sequence listings for two artificial sequences according to the invention are included in the text and in a separate sequence listing. The invention will be better understood by reference to the following detailed description in connection with the accompanying drawings.

BRIEF DESCRIPTION OF THE DRAWINGS

FIG. 4 is a table illustrating experimental results of a Reed-Solomon correction on a set of 10-mer DNA sequences (SEQ ID NOS:4099, 3909, 3762, 3762, 4100, 697, 4101, 1316, 1928, 1928, 1515, 1515, 4102, 2378, 2378, 4016, 4016, 4103, 1708, 4104, 3608, 3970, 3970, 1316, 1316, 4105 and 2346, respectively).

DETAILED DESCRIPTION OF THE INVENTION

A genome is not random. A genome is a form of an oriented linear heteropolymer that contains overlapping structures and duplicates in monomer subunit sequences, all of which are built out of a limited set of base pairs, typically denominated C, G, A and T. Some genomes are circular. Thus one can say that for those, the circle can be opened and an arbitrary point and thus be treated as a linear genome. These characteristics can be exploited in the process of genome sequencing. Other constructs in this category include amino acids, monomer subunits as a sequence of nucleotides and artificial DNA sequences comprising at least one oligonucleotide. All of these constructs may be processed as hereinafter explained.

Figure 1:
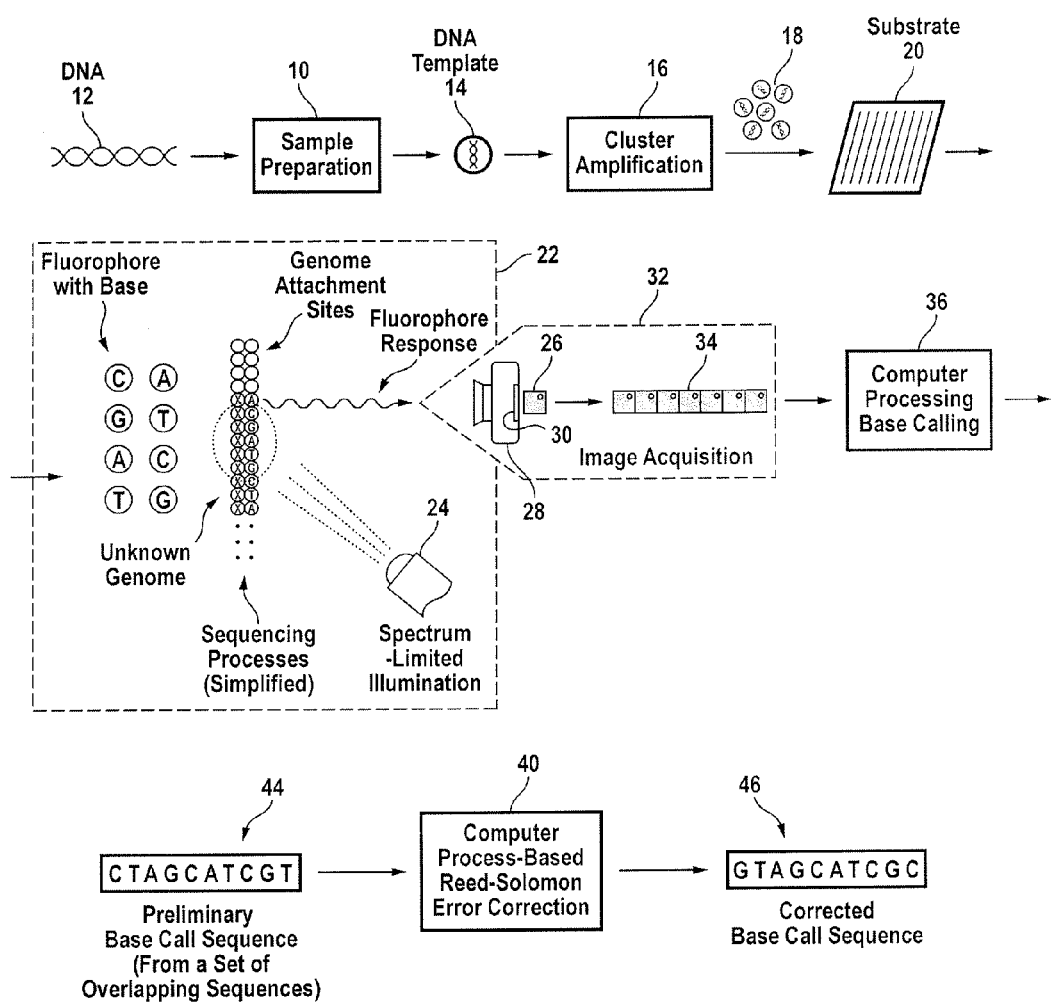
FIG. 1 is a block diagram of an environment that may employ a process according to the invention, which shows preliminary base call sequence=SEQ ID NO:4097 and corrected base call sequence=SEQ ID NO:4098.

Referring to FIG. 1, the overall method for sequencing target nucleic acids, which has been explained in detail elsewhere, includes sample preparation 10 involving extracting and fragmenting target nucleic acids from a DNA sample 12 to produce fragmented target nucleic acid templates 14 that will generally include one or more adaptors. The target nucleic acid templates 14 are optionally subjected to amplification methods 16 to form nucleic acid nanoballs, herein DNBs 18, which are typically disposed on a surface or substrate 20 for purpose of analysis. The substrate may yield patterned or random arrangements of DNBs. Nucleotide sequencing processes 22 are performed on the nucleic acid nanoballs, typically through sequencing-by-ligation techniques, including combinatorial probe anchor ligation ("cPAL") methods, which are described, for example, in Drmanac et al., "Human Genome Sequencing Using Unchained Base Reads on Self-Assembling DNA Nanaoarrays," *Science* 327:78-81, 2009 (Jan. 1, 2010), as well as in published PCT patent applications WO07/133831, WO06/138257, WO06/138284, WO07/044245, WO08/070352, WO08/058282, WO08/070375; and published U.S. patent applications 2007-0037152 and 2008-0221832. In such methods, known labels, such as specific fragments containing a single molecule of a distinguishable fluorophore, are attached as labels according to well-understood rules to the target nucleic acid templates, then resequence indexed on the same types of DNA strand to provide the basis of overlapping data. The sequencing processes 22 referred to herein are merely representative. In another embodiment, tagging is employed. Other processing techniques known or developed in the art may be employed. Then the collection of DNBs on the substrate is irradiated with radiation 24 to excite the fluorophores sufficient to cause the fluorophores associated with each specific label C, G, A or T to fluoresce at their unique wavelengths, from which a spatial image 26 can be made by a camera 28, on a (standard or time-delay integration TDI) CCD array or a scanner in lieu of a CCD array, or other electronic current/voltage sensing techniques. Other sensing mechanisms, such as impedance change sensors, may also be employed. The irradiation may be spectrum specific to excite only a selected fluorophore at a time, which can then be recorded by the camera, or the input to the camera 30 may be filtered to sense and record only spectrum-specific received fluorescent radiation, or all fluorescent radiation can be sensed and recorded simultaneously on a color LCD array and then later analyzed for spectral content at each interrogation site in which there is a nucleic acid construct. The image acquisition 32 yields a series 34 of images of a plurality of interrogation sites that can be analyzed based on spectrum-specific fluorescence intensity through computer processing of the levels of intensity in a process herein denoted as base calling 36 and explained in greater detail herein below. The cPAL and other sequencing methods can also be used to detect specific sequences, such as including Single Nucleotide Polymorphisms ("SNPs") in nucleic acid constructs, (which include nucleic acid nanoballs as well as linear and circular nucleic acid templates). The calls, or identification of the sequences of base calls, e.g., base calls 44 (herein shown not as overlapping), may contain errors for reasons evident by the nature of the sequencing procedure. Using the computer process-based Reed-Solomon error correction 40 of the invention, whether in the form of a computer processor perform a Reed-Solomon algorithm or in the form of a comparison mechanism using precomputed expected base call sequences, such as in a look-up table, errors can be identified, "nocall" sequences can be flagged and corrections can be made to yield corrected base call sequences 46. It should be understood that the magnitude of the sites and structures herein depicted are merely a minute fraction of the magnitude of the sites and structures analyzed on a substrate 20, as they do not easily admit to illustration. For example the substrate may be a photolithographically etched, surface modified (SOM) 25 mm by 75 mm silicon substrate with grid-patterned arrays of about 300-nm spots for DNB binding to increase DNA content per array and improve image information density as compared to random genomic DNA arrays.

Sequencing probes may be detectably labeled with a wide variety of labels. Although the foregoing and following description is primarily directed to embodiments in which the sequencing probes are labeled with fluorophores, it will be appreciated that similar embodiments utilizing sequencing probes comprising other kinds of labels are encompassed by the present invention. Moreover, the processes according to the invention can be employed with unlabeled structures.

Multiple cycles of cPAL (whether single, double, triple, etc.) will identify multiple bases in the regions of the target nucleic acid adjacent to the adaptors. (It is possible to employ a single cycle of cPAL to render multiple bases in an alternate design.) In brief, cPAL methods are repeatedly executed for interrogation of multiple bases within a target nucleic acid by cycling anchor probe hybridization and enzymatic ligation reactions with sequencing probe pools designed to detect nucleotides at varying positions removed from the interface between the adaptor and target nucleic acid. In any given cycle, the sequencing probes used are designed such that the identity of one or more of the bases at one or more positions is correlated with the identity of the label attached to that sequencing probe. Once the ligated sequencing probe (and hence the base or bases at the interrogation position or positions are detected, the ligated complex is stripped off of the DNB and a new cycle of adaptor and sequencing probe hybridization and ligation is conducted. By this mechanism, oversampled data are obtainable. Oversampling is done by sequencing more cycles than needed to decode an N-mer.

Four different fluorophores are typically used to identify a base at an interrogation site within a sequencing probe. Conventionally a single base is queried per hybridization-ligation-detection cycle. However, as will be appreciated, embodiments utilizing 8, 16, 20 and 24 fluorophores or more are also encompassed by the present invention. Increasing the number of fluorophores, or using shades of the same fluorophores, or using a combination of the fluorophores increases the number of bases that can be identified during any one cycle.

In one exemplary embodiment, a set of 7-mer pools of sequencing probes is employed having the following structures, according to conventional notation:

```
3'-F1-NNNNNNAp

3'-F2-NNNNNNGp

3'-F3-NNNNNNCp

3'-F4-NNNNNNTp
```

The "p" represents a phosphate available for ligation and "N" represents degenerate bases. F1-F4 represent four different fluorophores—each fluorophore is thus associated with a particular base, A, G, C or T. This exemplary set of probes would allow detection of the base immediately adjacent to the adaptor upon ligation of the sequencing probe to an anchor probe hybridized to the adaptor. To the extent that the ligase used to ligate the sequencing probe to the anchor probe discriminates for complementarity between the base at the interrogation position of the probe and the base at the detection position of the target nucleic acid, the fluorescent signal that would be detected upon hybridization and ligation of the sequencing probe provides the identity of the base at the detection position of the target nucleic acid. In some embodiments, a set of sequencing probes will comprise three differentially labeled sequencing probes, with a fourth optional sequencing probe left unlabeled.

After performing a hybridization-ligation-detection cycle, the anchor probe-sequencing probe ligation products are stripped and a new cycle is begun. The accuracy of identification of bases and by extension the number of bases that can be consistently and accurately identified can be increased using the error correction methods described herein.

Imaging acquisition may be performed using methods known in the art, including the use of commercial imaging packages such as Metamorph (Molecular Devices, Sunnyvale, Calif.). Data extraction may be performed by a series of binaries written in, e.g., C/C++ and base-calling and read-mapping may be performed by a series of Matlab and Perl scripts.

In an exemplary embodiment, DNBs disposed on a surface undergo a cycle of cPAL in which the sequencing probes utilized are labeled with four different fluorophores (each corresponding to a particular base at an interrogation position within the probe). In a preferred embodiment, to determine the identity of a base of each DNB disposed on the surface, each field of view ("frame") is imaged with four different wavelengths corresponding to the four fluorescently labeled sequencing probes. All images from each cycle are saved in digital form in a cycle directory, where the number of images is four times the number of frames (where four fluorophores are used). Cycle image data can then be saved into a directory structure organized for downstream processing.

In some embodiments, data extraction will rely on two types of image data: bright-field images to demarcate the positions of all DNBs on a surface, and sets of fluorescence images acquired during each sequencing cycle. Data extraction software can be used to identify all objects with the bright-field images and then for each such object, the software can be used to compute an average fluorescence value for each sequencing cycle. For any given cycle, there are four data points corresponding to the four images taken at different wavelengths to query whether that base is an A, G, C or T. These raw data points (also referred to herein as "base calls") are consolidated, yielding a discontinuous sequencing read for each DNB. This read may contain errors due to the ambiguity of the decision-making process in the base call.

Therefore, according to the invention, error correction 40 is invoked to yield corrected base calls 46. The error correction processes use a class of linear block cyclic symbol-based error correction methods. The methods are based on the use of run-length limited codes of the type known as the Reed-Solomon codes. Reed-Solomon codes have been explained at length in the mathematics and communication literature. Reference is made to the seminal paper "Polynomial Codes Over Certain Finite Fields," by I. S. Reed and G. Solomon, *SIAM Journal of Applied Math.*, vol. 8, 1960, pp. 300-304 for the mathematical basis. Further reference is made to textbooks for an explanation of the implementation, such as *Digital Communications: Fundamentals and Applications, Second Edition*, by Bernard Sklar (Prentice-Hall, 2001). A brief tutorial on the use of Reed-Solomon codes based on an explanation by Sklar is provided as follows.

Reed-Solomon codes are nonbinary cyclic codes with symbols made up of m-bit sequences, where m is any positive integer having a value greater than 2. RS(n, k) codes on m-bit symbols exist for all n and k for which $$0 < k < n < 2^m + 2 \quad (1),$$

where k is the number of data symbols being encoded, and n is the total number of code symbols in the encoded block. For the most conventional Reed-Solomon, or RS(n, k) code, $$(n,k) = (2^m - 1, 2^m - 1 - 2t) \quad (2)$$

where t is the symbol-error correcting capability of the code, and n−k=2t is the number of parity symbols. An extended Reed-Solomon code can be made up with $n=2^m$ or $n=2^m+1$, but not any further.

Reed-Solomon codes achieve the largest possible code minimum distance for any linear code with the same encoder input and output block lengths. For nonbinary codes, the distance between two code words is defined as the number of symbols in which the sequences differ. For Reed-Solomon codes, the code minimum distance is given by:

$$d_{min} = n - k + 1 \quad (3)$$

The code is capable of correcting any combination of t or fewer errors, where t can be expressed as:

$$t = \lfloor (d_{min} - 1)/2 \rfloor = \lfloor (n-k)/2 \rfloor \quad (4)$$

where the center portion of this equation "x" means the largest integer not to exceed x. Equation (4) illustrates that for the case of Reed-Solomon codes, correcting t symbol errors requires no more than 2t parity symbols. Equation (4) lends itself to the following intuitive reasoning. One may say that the decoder has n−k redundant symbols to "spend," which is twice the amount of correctable errors. For each error, one redundant symbol is used to locate the error, and another redundant symbol is used to find its correct value. The correction is known as an erasure, which is equivalent to a no-call-correcting capability.

The erasure or no-call-correcting capability ρ of the code is:

$$\rho = d_{min} - 1 = n - k \quad (5)$$

Simultaneous error-correction and erasure-correction capability can be expressed as follows:

$$2\alpha + \gamma < d_{min} < n - k \quad (6)$$

where α is the number of symbol-error patterns that can be corrected and γ is the number of symbol erasure patterns that can be corrected. An advantage of nonbinary codes such as a Reed-Solomon code can be seen by the following comparison. Consider a binary (n, k)=(7, 3) code. The entire n-tuple space contains $2n=2^7=128$ n-tuples, of which $2k=2^3=8$ (or 1/16 of the n-tuples) are code words. Next, consider a nonbinary (n, k)=(7, 3) code where each symbol is composed of m=3 bits. The n-tuple space amounts to $2nm=2^{21}=2,097,152$ n-tuples, of which $2km=2^9=512$ (or 1/4096 of the n-tuples) are code words. When dealing with nonbinary symbols, each made up of m bits, only a small fraction (i.e., 2km of the large number 2nm) of possible n-tuples are code words. This fraction decreases with increasing values of m. The important point here is that when a small fraction of the n-tuple space is used for code words, a large $d_{min}$ can be created.

Reed-Solomon codes have the remarkable property that they are able to correct any set of n−k symbol erasures within the block, erasure being equivalent to a no-call. Reed-Solomon codes can be designed to have any redundancy. However, the complexity of a high-speed implementation increases with redundancy. Thus, the more attractive Reed-Solomon codes have high code rates (low redundancy).

Referring now a specific implementation of the invention, Reed-Solomon error detection and Reed-Solomon error correction is based on selection and use of a specific error-correcting code that in general works by oversampling a polynomial constructed from the data. In the present context, the coefficients of the polynomial are the base call designations from fluorophore-label identification in the base calling analysis coded as integers, e.g., 1,2,3,4, which has been made redundant in nature by the overlapping probes, where the redundancy comes from the length of the probes. As noted, sampling the polynomial more often than is necessary makes the polynomial over-determined. So long as more than a minimum number of the samples is correct, the original polynomial can be recovered in the presence of some bad points. As noted, the relationship between good and bad points determines the number of errors that can be corrected, which for k bases, with n−k redundant bases, have the following properties: where 2t=n−k and the location of the error is not known, t errors can be identified and corrected. Where location of the errors is known, then 2t errors can be corrected. In other words, Reed-Solomon methodology can correct half as many errors as there are redundant symbols in a block when location of errors is not known and if location is known, it can correct as many errors as there are redundant symbols. The method according to the invention relies on generating a correction code set wherein each random pair from the code set is guaranteed to have a minimum ratio R of distance D to length L of greater than 20 percent from every other member of the set. The distance D greater than or equal to 3 for length L equal to 10, namely a 10 base code. Similarly the distance D greater than or equal to 3 for length L equal to 7, namely a 7 base code.

Location of errors can be identified by base reference to the base calling quality score. the base calling quality score can be obtained directly from commercially available base calling algorithms. A paper describing one commercially available technique was newly published in the aforementioned Drmanac et al., "Human Genome Sequencing Using Unchained Base Reads on Self-Assembling DNA Nanaoarrays," *Science*, Vol. 327, pp. 78-81, Jan. 1, 2010 (also found online at www.scienceexpress.org, dated 5 Nov. 2009, Page 1 (10.1126/science.1181498.) This paper is incorporated herein by reference.

Significantly, since Reed-Solomon block codes can correct block errors, it can therefore be used to correct for errors in base identification, unlike Hamming block codes, which can correct only for bit errors.

For DNA reading applications, it is typically thought desirable that the value of "n" be kept small, since the value of "n" ultimately defines the number of bases in the final code, and the value needs to be small to minimize the cost of the assay. Further, the probability of a base read cannot be so high that the sequencing technology cannot be enabled. In the most efficient case, the value of t, the number of errors that is to be corrected in any one iteration, is set to "1". In a further case, 10-base codes may be provided that are able to correct 2 errors. Thus, the artifical 10-mer set that can correct for two errors is as follows:

| | |
|---|---|
| CAGCAAGCAG | (SEQ ID NO: 1551) |
| GGAGAAAACG | (SEQ ID NO: 9) |
| CGGGAACAAA | (SEQ ID NO: 257) |
| CACCCACAGC | (SEQ ID NO: 266) |
| AACAGACGAC | (SEQ ID NO: 2342) |
| TTTAACATGC | (SEQ ID NO: 3128) |
| TCTCACCAGT | (SEQ ID NO: 319) |
| CCAACCCAGA | (SEQ ID NO: 325) |
| AGCCCCAGGG | (SEQ ID NO: 2131) |
| GCCGCCCGAC | (SEQ ID NO: 2396) |
| CGCAGCAAAG | (SEQ ID NO: 94) |
| ACACGCCGAA | (SEQ ID NO: 2408) |
| TGGGTCTTAC | (SEQ ID NO: 3955) |
| CAAAAGCAAG | (SEQ ID NO: 377) |
| GAGAAGAACA | (SEQ ID NO: 127) |
| TGTAAGAGCT | (SEQ ID NO: 2182) |
| ACCACGCACG | (SEQ ID NO: 393) |
| CGACCGAGCA | (SEQ ID NO: 2197) |
| GGGCCGCGAG | (SEQ ID NO: 2459) |
| ACGGCGAGGC | (SEQ ID NO: 2204) |
| TGTGCGGCAT | (SEQ ID NO: 1698) |
| CTGGGGCTAT | (SEQ ID NO: 3494) |
| TCCCTGTTAG | (SEQ ID NO: 4023) |
| TTCTATCAGC | (SEQ ID NO: 456) |
| TTGTCTGCAG | (SEQ ID NO: 1761) |
| CGTTGTCTAG. | (SEQ ID NO: 3563) |

The hardware basis for implementing Reed-Solomon codes has been detailed elsewhere for communication applications. Reference is made to "Reed-Solomon Error Correction," by C. K. P. Clarke, *BBC Research & Development White Paper WHP* 031, July 2002, (British Broadcasting Corporation), incorporated by reference herein for all purposes and attached hereto for convenience as Appendix A. This white paper describes the principles of a general purpose hardware implementation of an error correcting device using Reed-Solomon coded data as input. In the present context, once a polynomial has been constructed from the DNA base call data, it is processed by circuitry such as that disclosed by Clarke to recover the DNA tags.

It should be understood that the implementation of this invention is only practical in the context of use of a dedicated or a general purpose computer processor. In addition to a hardware implementation of the Reed-Solomon decoder as described in Appendix A, a Reed-Solomon-code-based decoder may also be implemented through a computer program of a general-purpose digital computer. Representative source code that is in MATLAB source code form (MATLAB 7.9.0/529 (R2009b) for representative Reed-Solomon code designs is set forth below. This includes a 10 10 base code design with one error correction capability and a 7 base R-S decoder:

---
10 10base code design
---

```
v.m = 4;      % Number of bits per symbol
v.n = 2^v.m−1; % Codeword length
v.k = 13;
v.n0 = 10;
v.s = v.n − v.n0;
v.k0 = v.k − v.s;
v.t = (v.n−v.k)/2;  % Error-correction capability of the code
% Coder/Decoder Construction
coder = fec.rsenc(v.n, v.k);
coder.ShortenedLength = v.s;
decoder = fec.rsdec(coder);
%% Construct full data set
v.data0 = fullfact(4*ones(1,v.k0));
v.nwords0 = size(v.data0,1); % number of words to process
%% Construct message
v.send0 = encode(coder, v.data0')'; % Encode the data.
%% Select the valid codes
v.valid = all(ismember(v.send0,[1 2 3 4]),2);
v.data = v.data0(v.valid,:);
v.nwords = size(v.data,1);
v.send = v.send0(v.valid,:);
v.seq = int2nt(v.send);
```

---
Reed-Solomon Decoder (7base)
---

```
function [decoded_integer, decoded0_integer, status, recovery] =
reed_solomon_decoder_7base(sequence_corrupted_integer, erasures)
v.m = 3;    % Number of bits per symbol
v.n = 2^v.m−1; % Codeword length
v.k = 5;    % message length
v.t = (v.n−v.k)/2;  % Error-correction capability of the code
% Coder/Decoder Construction
coder = fec.rsenc(v.n, v.k);
decoder = fec.rsdec(coder);
u.seq_corrupted_integer = double(sequence_corrupted_integer);
u.erasures = erasures;
[dummy, nerrors, seq_corrected_integer] = decode(decoder,
     u.seq_corrupted_integer', u.erasures'); % Decode the noisy code.
u.seq_corrected_integer = seq_corrected_integer';
u.nerrors = nerrors';
recovery = (u.nerrors==1);
u.status = all(ismember(u.seq_corrected_integer,[1:4]),2) &
     ismember(u.nerrors,[0:v.t]);
decoded0_integer = u.seq_corrected_integer;
decoded_integer = decoded0_integer;
status = u.status;
decoded_integer(status==0,:) = 0;
```

The foregoing source code is applicable to each dataset below, including the following dataset for Reed-Solomon 6+4 base, 26 sequence, 2 base error correction, 4 nocall correction (SEQ ID NOS:1551, 9, 257, 266, 2342, 3128, 319, 325, 2131, 2396, 94, 2408, 3955, 377, 127, 2182, 393, 2197, 2459, 2204, 1698, 3494, 4023, 456, 1761, and 3563, respectively):

```
CAGCAAGCAG GGAGAAAACG CGGGAACAAA CACCCACAGC

AACAGACGAC TTTAACATGC TCTCACCAGT CCAACCCAGA

AGCCCCAGGG GCCGCCCGAC CGCAGCAAAG ACACGCCGAA

TGGGTCTTAC CAAAAGCAAG GAGAAGAACA TGTAAGAGCT

ACCACGCACG CGACCGAGCA GGGCCGCGAG ACGGCGAGGC

TGTGCGGCAT CTGGGGCTAT TCCCTGTTAG TTCTATCAGC

TTGTCTGCAG CGTTGTCTAG
```

The foregoing code set is also applicable to the following dataset for Reed-Solomon 8+2 base, 4096 sequence, 1 base error, 2 nocall correction (SEQ ID NOS:1-4096):

```
TAAAAAAAGG ATGAAAAACC CCACAAAAGC AGACAAAATT

CTACAAAATA ACCCAAAAGA ATCCAAAATC TGTCAAAATA

GGAGAAAACG AGGGAAAACA TGGGAAAAAG CTGGAAAACT

GGTGAAAAAT ACTTAAAACC ACAACAAAGC CGAACAAATT

ATAACAAATA CCCACAAAGA CTCACAAATC GTGACAAATG

TTTACAAATT GTCCCAAACG CTGCCAAACC GGTCCAAAAC

CCAGCAAAGT AGAGCAAATC CGCGCAAATA ATCGCAAATT

TAATCAAAAT GAGTCAAACT TCGTCAAATT AATTCAAAAA

TATTCAAACG GCTTCAAATG AGAAGAAACG TGAAGAAAAA

GGGAGAAACA AGTAGAAAAT CTTAGAAAAA GCACGAAAGT

GGCCGAAATA TTAGGAAAAC TGCGGAAAAT CTCGGAAACG

TAGGGAAAGA GTGGGAAACC CGTGGAAAAC CAATGAAATA

AACTGAAATC CCGTGAAAAA CCCATAAACT GATATAAATC

TCTATAAACC CAACTAAAAT CCGCTAAATT AGGCTAAAGC

CATCTAAACG CCAGTAAACA ACCGTAAACC AAATTAAAGG

GTATTAAAAC GGCTTAAAAT GAGTTAAAGA TTGTTAAACC

AAAAACAAGC GTAAACAAAG CACAACAAGA CGGAACAAAT

ATGAACAAAA TTGAACAACG GTTAACAACT TTCCACAATG

CAAGACAAGT AGGGACAAAC TCATACAAAT TAGTACAATT

GCGTACAACT GATTACAATG ACTTACAAAA TCTTACAACG

TCAACCAAGG CAACCCAAGC AACCCCAAGA AGGCCCAAAT

CTGCCCAAAA GGTCCCAACA TGAGCCAATG CTTGCCAATG

GTATCCAAGT GGCTCCAAGC CGGTCCAAGG AATTCCAACC

TGAAGCAACC CGCAGCAAAG TTCAGCAACT GGGAGCAAAC

CTTAGCAACC TTGCGCAATT GTTCGCAATG GAAGGCAAGC

ATAGGCAAAG TTAGGCAACA GTGGGCAAAA CGTGGCAACA

ATTGGCAACT TACTGCAATG GCCTGCAACG CCGTGCAACC

ACAATCAAAT AAGATCAATT ACTATCAACG TCTATCAAAA

AACCTCAACT TGGCTCAAGG GGTCTCAAGT CCAGTCAAAC

GACGTCAATG ACCGTCAAAA TCCGTCAACG CAGGTCAATC

TAATTCAAGC GTATTCAACA ATGTTCAACG TTGTTCAAAA

AAAAGAACG TAAAAGAAAA GAGAAGAACA TCGAAGAATA

TTGAAGAAGC AATAAGAAAT GACCAGAATA ACCCAGAAAG

TCCCAGAACA TACGAGAAAT TGGGAGAAGA CATGAGAAAC

CGATAGAATA ATATAGAATT CCCTAGAAGT AGCTAGAATC

TCTTAGAAGC TTTTAGAATA GAAACGAATC TCAACGAACC

CCCACGAAAG GCGACGAAAC CAACCGAACG TACCCGAAAC

CATCCGAAAT CCTGCGAACA GGCTCGAACG CGGTCGAACC

AATTCGAAGG GTTTCGAAAC TGAAGGAAGG CTTAGGAAGG

AAACGGAATT ACGCGGAAAT TATCGGAATA GCTCGGAACA

GAAGGGAACG TCAGGGAATG AAGGGGAACA TAGGGGAAAG

GATGGGAAAT GCCTGGAAGC GTCTGGAATA CCGTGGAAGG

TTAATGAATT TGCATGAATC ACTATGAAGC CGTATGAATT

ATTATGAATA GGACTGAAAC GTCCTGAAAT TGGCTGAACC

TCCGTGAAGC TTCGTGAATA CCTGTGAAGT AGTGTGAATC

AAATTGAAAA TAATTGAACG GCATTGAATG CACTTGAAAC

GAGTTGAAAG ACGTTGAATA ATGTTGAAGC TATTTGAAAT

GCTAATAAGA GTTAATAATC AGACATAAAA TGACATAACG

CTACATAAAT CGCCATAAAC GGGCATAAAG TGTCATAAAT

CTTCATAACG GGTGATAATA GAATATAAAC ATATATAAGG

CCCTATAATG TAGTATAACC GCGTATAATC GTGTATAAGA

CGAACTAAAA ATAACTAAAT AGCACTAAAC ATTACTAACG

TTTACTAAAA CTAGCTAAAC CGCGCTAAAT ATCGCTAAAA

TTCGCTAACG CAGGCTAAGA TGTGCTAAAC TAATCTAATA

GCATCTAACA ACGTCTAACG TCGTCTAAAA AATTCTAATT

TGAAGTAATT TCCAGTAAGA TTCAGTAATC AGTAGTAATA

CTTAGTAATT AAACGTAAGG GTACGTAAAC GGCCGTAAAT

GAGCGTAAGA TTGCGTAACC TCAGGTAAGT TGCGGTAATA

ACTGGTAAGA ATTGGTAATC CAATGTAAAT CCGTGTAATT

AGGTGTAAGC CATTGTAACG TTAATTAAGG AAGATTAACC

CGTATTAAGG CAACTTAATA AACCTTAATC CCGCTTAAAA

CAGGTTAACT CCTGTTAATG GCATTTAAGT GGCTTTAATA

CAAAAACAGA AACAAACAGC GTCAAACAAG CTGAAACAAC

GGTAAACACC TTACAACATG CGTCAACATG CACGAACAGT

CGGGAACAAA ATGGAACAAT TATGAACAGC GTTGAACACA

TCCTAACAAT CCTTAACAAC TCCACACAGG AGTACACATG

AAACCACAGA CACCCACAGC GAGCCACAGG ATGCCACAAC

TATCCACAGT TGCGCACATG ACTGCACAGG GGATCACAGC

GTCTCACAGT CATTCACACA CGAAGACAAG TTAAGACACT

TGCAGACACC GTGAGACAAT CGTAGACACT ATTAGACACA

TTTAGACAAG TGGCGACATC GACGGACAGC ATCGGACAAG
```

-continued

```
TTCGGACACA CAGGGACAGG AGTGGACACC TAATGACATG
GCATGACACG ACGTGACACA TCGTGACAAG GCTTGACAAT
ACCATACAAT AAACTACACT AATCTACAAG TATCTACACA
GCTCTACATA GTTCTACAGC GAAGTACATG ACAGTACAAA
TCAGTACACG CCCGTACAAC AAGGTACATA GCGGTACAAG
TCTGTACAAT TACTTACAGC GTCTTACACA CATTTACAGT
TACAACCAGG AGGAACCACT CTGAACCACA GGTAACCAAA
ACACACCAGA ATACACCATC CCCCACCAGC AGCCACCATT
CTCCACCATA GCGCACCAGG TCTCACCAGT GGCGACCACG
CGGGACCACC AATGACCAGG GTTGACCAAC CCTTACCACA
CCAACCCAGA CTAACCCATC ACCACCCAGC CGCACCCATT
ATCACCCATA TGTACCCATC GTACCCACG CGGCCCCACT
ATGCCCCACA TTGCCCCAAG GTTCCCCAAT CGAGCCCATA
ATAGCCCATT CCCGCCCAGT AGCGCCCATC TCTGCCCAGC
TTTGCCCATA TACTCCCAAT TGGTCCCAGA CATTCCCAAC
AGCAGCCACG TGCAGCCAAA TAGAGCCAGT GATAGCCAGG
ATTAGCCAAC GGACGCCATA GCCCGCCAGT AGGCGCCATG
TGAGGCCAAT CTAGGCCACG TTCGGCCAAC GGGGGCCACT
AGTGGCCAAA TGTGGCCACG CTTGGCCAAT AAATGCCATC
CACTGCCATA ACGTGCCAAC CCAATCCACT CCTATCCAAG
CACCTCCAAT CGGCTCCAGA ATGCTCCAGT TATCTCCAAC
ACAGTCCACC CCCGTCCACA GGATTCCAAT AACTTCCAGG
GTCTTCCAAC TGGTTCCACT CTGTTCCAAG GGTTTCCACG
CAAAAGCAAG TACAAGCACC GCCAAGCATC GTCAAGCAGA
CCGAAGCATG CATAAGCACT TCACAGCAAC CCCCAGCACG
TAGCAGCATC GCGCAGCACC GTAGAGCAGT GGCGAGCAGC
CGGGAGCAGG AATGAGCACC TGATAGCATG CTTTAGCATG
ACCACGCACG TCCACGCAAA AAACCGCAAG TAACCGCACA
GCACCGCATA GTACCGCAGC GGCCCGCAGT GAGCCGCAAA
ACGCCGCATG AATCCGCACT TCAGCGCAAT TAGGCGCATT
GCGGCGCACT GATGCGCATG ACTGCGCAAA TCTGCGCACG
CAATCGCAGT AGGTCGCAAC CGAAGGCAGA ATAAGGCAGT
CCCAGGCATT AGCAGGCAGC GATAGGCACC TCTAGGCATC
TTTAGGCAGA CCGCGGCACT CATCGGCATG CCAGGGCATA
CTAGGGCAGC ACCGGGCATC CGCGGGCAGT ATCGGGCAGA
CAGGGGCAAA TGTGGGCAGC TCGTGGCAGA TTGTGGCATC
AGAATGCATG GGGATGCATA TAACTGCAGT GGCCTGCACA
AATCTGCAGA ACAGTGCAGG CTCGTGCATG GCGGTGCAGA
GTGGTGCATC CAATTGCACA AACTTGCACC GGTTTGCAGC
CCGAATCAGT AGGAATCATC CGACATCACA ATACATCACT
AGCCATCACC GATCATCAGC ATTCATCAAG TTTCATCACA
```

```
GTAGATCATG ACGGATCAGC CGGGATCATT ATGGATCATA
TGATATCAGT GACTATCACA TCCTATCATA TTCTATCAGC
AGTTATCAGA CTTTATCAGT AGAACTCACA TGAACTCAAG
CTAACTCACT CGCACTCACC GGGACTCACG TGTACTCACT
CTTACTCAAG GGCCCTCATG ACGCCTCAGT CGGCCTCATC
ATAGCTCACC AGCGCTCACT CTCGCTCACA TAGGCTCAGG
GATGCTCAGT CAATCTCATG GCCTCTCAAC CCGTCTCAAG
ATAAGTCATG CCCAGTCAGG GCGAGTCAGC GTGAGTCATA
TACCGTCAGC GTCCGTCACA CATCGTCAGT CGCGGTCATG
GGGGGTCATC AAATGTCACT AATTGTCAAG TATTGTCACA
GCTTGTCATA GTTTGTCAGC CCAATTCATC AGAATTCAGT
CTAATTCAGA GACATTCAAG ACCATTCATA ATCATTCAGC
CAGATTCAAC TGTATTCAGA TAACTTCATG GCACTTCACG
ACGCTTCACA TCGCTTCAAG GCTCTTCAAT ACAGTTCATT
CGAGTTCAGC AGCGTTCAGA CTCGTTCAGT AAGGTTCAAT
GATGTTCACA TCTGTTCATA TTTGTTCAGC TGGTTTCATC
GAAAAGACA TCAAAGATA TTAAAGAGC TGCAAAGAGT
AAGAAAGACG TAGAAAGAAA ACTAAAGATT CGTAAAGAGC
AACCAAGATG GCCCAAGAAA TGAGAAGAGA GACGAAGACT
TCCGAAGATT CCTGAAGATC AGTGAAGAGT CTTGAAGAGA
CGGTAAGATA ATGTAAGATT GCAACAGAAC CACACAGATG
GAGACAGATC TCGACAGACC GACCCAGACC TCCCCAGATC
TTCCCAGAGA CAGCCAGACG CCTCCAGATT AGTCCAGAGC
CGATCAGACC AGCTCAGACA TGCTCAGAAG CTCTCAGACT
GATTCAGAGA TTTTCAGACC AACAGAGACT TGGAGAGAGG
GGTAGAGAGT ACACGAGAAT AAGCGAGATT ACTCGAGACG
TCTCGAGAAA AAAGGAGACA TAAGGAGAAG CACGGAGACC
GAGGGAGACG TCGGGAGATG TATGGAGACT GCTGGAGATT
CCATGAGAGG ATCTGAGATG TTGATAGATT GTTATAGATG
TGACTAGACC CGCCTAGAAG TTCCTAGACT GGGCTAGAAC
CTTCTAGACC GAATTAGAAG ACATTAGATA ATATTAGAGC
CCCTTAGATC AGCTTAGAGT CTCTTAGAGA AAGTTAGAAA
TAGTTAGACG GCGTTAGATG GATTTAGACT TCTTTAGATT
GAAAACGAAC ATAAACGAGG CCCAACGATG TAGAACGACC
GCGAACGATC GTGAACGAGA TACCACGATC GCCCACGACC
CCGCACGACG CATCACGATT CGCGACGAGG GGGGACGAGC
GCTTACGAGA GTTTACGATC TAAACCGATA GCAACCGACA
ACGACCGACG TCGACCGAAA AATACCGATT CTACCCGAGG
GACCCGAAA ACCCCCGATG GGGCCCGAGT TGTCCCGAGG
TACGCCGATT GCCGCCGACT CATGCCGATC CGATCCGAAA
```

-continued

```
ATATCCGAAT AGCTCCGAAC ATTTCCGACG TTTTCCGAAA
CAAAGCGAAT CCGAGCGATT AGGAGCGAGC CATAGCGACG
CCCCGCGACT GATCGCGATC TCTCGCGACC AAAGGCGAAC
GTAGGCGAGG CACGGCGAAA ACGGGCGATC CGGGGCGAGT
ATGGGCGAGA TGATGCGATT TCCTGCGAGA TTCTGCGATC
AGTTGCGATA CTTTGCGATT GCAATCGAGT GGCATCGATA
AGACTCGACG TGACTCGAAA GGGCTCGACA AGTCTCGAAT
CTTCTCGAAA GGAGTCGATT GCCGTCGAGA GTCGTCGATC
CTGGTCGATG TTATTCGAGG AAGTTCGACC CGTTTCGAGG
ATAAAGGACC AGCAAGGACT CTCAAGGACA TAGAAGGAGG
GATAAGGAGT GCCCAGGAGG CCGCAGGAGC AGGCAGGATT
CTGCAGGATA AGAGAGGACA TGAGAGGAAG CTAGAGGACT
CGCGAGGACC GGGGAGGACG TGTGAGGACT CTTGAGGAAG
GTAACGGATG ACGACGGAGC CGGACGGATT ATGACGGATA
CTACCGGACC CGCCCGGACT ATCCCGGACA TTCCCGGAAG
TGTCCGGACC CCGGCGGAGT AGGGCGGATC GAATCGGACT
TCATCGGATT TGCTCGGAGA TAGTCGGAAT GATTCGGAAG
ACTTCGGATA ATTTCGGAGC GGAAGGGACA TACAGGGAGT
AGGAGGGACG TGGAGGGAAA CATAGGGAGC AGCCGGGATG
GCGCGGGAGT TCTCGGGAGG TAAGGGAGA GTAGGGGACC
GGCGGGGACT TTGGGGGAAC AATGGGGAGT CCATGGGAAA
ACCTGGGAAC CAGTGGGATA GCTATGGAAC CCACTGGATT
AGACTGGAGC CGCCTGGAGA ATCCTGGAGT CAGCTGGAAT
CCGGTGGACA GAATTGGAGA TTATTGGACC TGCTTGGACT
CTCTTGGAAG AAGTTGGAGG GTGTTGGAAC CGTTTGGACC
TCAAATGAAT TAGAATGATT GCGAATGACT GATAATGATG
ACTAATGAAA TCTAATGACG GGACATGAGA TACCATGACT
GCCCATGATT AGGCATGAGG CATCATGACC ACCGATGACG
TCCGATGAAA AAATATGAGC GTATATGAAG CACTATGAGA
CGGTATGAAT ATGTATGAAA TTGTATGACG GTTTATGACT
GTAACTGAGT GGCACTGAGC CGGACTGAGG AATACTGACC
CCTCCTGAAA CAAGCTGAAG TACGCTGACC GCCGCTGATC
GTCGCTGAGA CCGGCTGATG CATGCTGACT TCATCTGAGG
TACAGTGATG GCCAGTGACG CCGAGTGACC GAACGTGAAG
ACACGTGATA ATACGTGAGC CCCCGTGATC AGCCGTGAGT
CTCCGTGAGA AAGCGTGAAA TAGCGTGACG GCGCGTGATG
GATCGTGACT TCTCGTGATT ACGGGTGACT AATGGTGATG
GCTGGTGAAA TGATGTGACC CGCTGTGAAG TTCTGTGACT
GGGTGTGAAC CTTTGTGACC TAAATTGAGC GTAATTGACA
ATGATTGACG TTGATTGAAA CCACTTGAGG ATCCTTGATG
GGAGTTGACC GTCGTTGACT TGGGTTGAAC CATGTTGAGA
```

```
ACATTTGAAT AAGTTTGATT ACTTTTGACG TCTTTTGAAA
GCAAAATAGA GTAAAATATC GGCAAATATT ACGAAATAGG
TGACAATAAT CTACAATACG TTCCAATAAC GGGCAATACT
AGTCAATAAA TGTCAATACG CTTCAATAAT GGAGAATATA
GCCGAATAGT AGGGAATATG GATTAATAAC ATTTAATAGG
ATAACATACG TTAACATAAA TAGACATAGC GTGACATACA
CGTACATAAA ATTACATAAT GCCCCATAGC GTCCCATATA
CCGCCATAGG TGAGCATAAC CGCGCATACG TTCGCATAAT
GGGGCATACC CTTGCATAAC AAATCATATT ACGTCATAAT
TATTCATATA GCTTCATACA AGAAGATATA CTAAGATATT
ACCAGATAGT CGCAGATATC GGGAGATATG TGTAGATATT
GGCCGATACG CGGCGATACC AATCGATAGG GTTCGATAAC
ACAGGATAGA ATAGGATATC CCCGGATAGC AGCGGATATT
CTCGGATATA GCGGGATAGG TCTGGATAGT CAATGATACG
TACTGATAAC CATTGATAAT CGAATATAGG GTGATATAGT
TTTATATAGG CATCTATATA CCAGTATATG GACGTATAAC
ATCGTATAGG CAGGTATAAG TCGTTATAGG GCTTTATAGT
TCGAACTAGC TTGAACTATA GACCACTAGC ATCCACTAAG
TTCCACTACA CAGCACTAGG AGTCACTACC TGGGACTATC
ACATACTATT CGATACTAGC AGCTACTAGA CTCTACTAGT
AAGTACTAAT GATTACTACA TCTTACTATA TTTTACTAGC
GAAACCTAGA TTAACCTACC TGCACCTACT CTCACCTAAG
AAGACCTAGG GTGACCTAAC CGTACCTACC TGGCCCTATT
GGTCCCTATG AGAGCCTAAG TGAGCCTACA GACGCCTAGT
GGGGCCTAAA AGTGCCTACT CTTGCCTACA GCTTCCTAAC
CCTAGCTAGG CACCGCTAGT CGGCGCTAAA ATGCGCTAAT
TATCGCTAGC GTTCGCTACA TTAGGCTATG CGTGGCTATG
GGATGCTAGT AACTGCTAAG TACTGCTACA GCCTGCTATA
GTCTGCTAGC CTGTGCTAGG GAAATCTACT TCAATCTATT
TGCATCTAGA TAGATCTAAT GATATCTAAG ACTATCTATA
ATTATCTAGC GCCCTCTAAT TGAGTCTAGT GACGTCTACA
TCCGTCTATA TTCGTCTAGC AGTGTCTAGA CTTGTCTAGT
GTATTCTATG ACGTTCTAGC CGGTTCTATT ATGTTCTATA
AAAAAGTATA GCAAAGTAAG CACAAGTATC GAGAAGTATG
ACGAAGTAAA TCGAAGTACG TATAAGTATT GCTAAGTACT
GACCAGTACG TCCCAGTATG CAGCAGTACC AGTCAGTAGG
AACGAGTATT CGATAGTACG TTATAGTAAT TGCTAGTAAC
GTGTAGTACT CGTTAGTAAT ATTTAGTAAA TTTTAGTACG
TTAACGTAGG AAGACGTACC CGTACGTAGG CAACCGTATA
AACCCGTATC CCGCCGTAAA CAGGCGTACT CCTGCGTATG
```

-continued

```
GCATCGTAGT GGCTCGTATA GACAGGTATT TCCAGGTACT
CCTAGGTACC TAACGGTAAT GAGCGGTACT TCGCGGTATT
AATCGGTAAA TATCGGTACG GCTCGGTATG GAAGGGTATA
ACAGGGTAAG TCAGGGTACA AAGGGGTATG GCGGGGTAAA
ACTGGGTACT GTCTGGTACG CTGTGGTACC GGTTGGTAAC
CGAATGTAAA ATAATGTAAT AGCATGTAAC ATTATGTACG
TTTATGTAAA CTAGTGTAAC CGCGTGTAAT ATCGTGTAAA
TTCGTGTACG CAGGTGTAGA TGTGTGTAAC TAATTGTATA
GCATTGTACA ACGTTGTACG TCGTTGTAAA AATTTGTATT
GGCAATTAAA GAGAATTAGT TATAATTAGG TGACATTATA
TCCCATTAGT CCTCATTAGC AGTCATTATT CTTCATTATA
GGAGATTAAT AACGATTAGG GTCGATTAAC TGGGATTACT
CTGGATTAAG GGTGATTACG ACATATTACC CCCTATTACA
TTAACTTATT TGCACTTATC ACTACTTAGC CGTACTTATT
ATTACTTATA GGACCTTAAC GTCCCTTAAT TGGCCTTACC
TCCGCTTAGC TTCGCTTATA CCTGCTTAGT AGTGCTTATC
AAATCTTAAA TAATCTTACG GCATCTTATG CACTCTTAAC
GAGTCTTAAG ACGTCTTATA ATGTCTTAGC TATTCTTAAT
AGAAGTTAAT CTAAGTTAAA GACAGTTAGG ATCAGTTAAC
CAGAGTTAGC AGTAGTTACG TGTAGTTAAA TCGCGTTAGG
GCTCGTTAGT CGAGGTTAAC AGCGGTTAAA TGCGGTTACG
CTCGGTTAAT AAGGGTTAGT TTTGGTTAAC CATTGTTATA
GAAATTTATC TCAATTTACC CCCATTTAAG GCGATTTAAC
CAACTTTACG TACCTTTAAC CATCTTTAAT CCTGTTTACA
GGCTTTTACG CGGTTTTACC AATTTTTAGG GTTTTTTAAC
TTAAAAACTG CGTAAAACTG CAACAAACGA AACCAAACGC
GTCCAAACAG CTGCAAACAC GGTCAAACCC CCTGAAACGG
TAATAAACCT GCATAAACTT GGCTAAACGA GAGTAAACAT
AATTAAACCA TATTAAACAG AAAACAACGA CACACAACGC
GAGACAACGG ATGACAACAC TATACAACGT TCCCCAACGG
AGTCCAACTG GGAGCAACAG AACGCAACGT AGGGCAACAA
TGGGCAACCG CTGGCAACAT GGTGCAACCT ACTTCAACAC
TGGAGAACTC CGACGAACAG TTACGAACCT TGCCGAACCC
GTGCGAACAT CGTCGAACCT ATTCGAACCA TTTCGAACAG
TCGGGAACGC TTGGGAACTA CCATGAACTC AGATGAACGT
CTATGAACGA GACTGAACAG ACCTGAACTA ATCTGAACGC
CAGTGAACAC TGTTGAACGA AAAATAACCT AATATAACAG
TATATAACCA GCTATAACTA GTTATAACGC ACCCTAACAT
CAAGTAACCC AACGTAACCA TACGTAACAG GGTGTAACGA
ATATTAACTG CCCTTAACGG GCGTTAACGC GTGTTAACTA
ACAAACACGA ATAAACACTC CCCAACACGC AGCAACACTT
```

-continued

```
CTCAACACTA GCGAACACGG TCTAACACGT TACCACACGG
AGGCACACCT CTGCACACCA GGTCACACAA AGAGACACTA
CTAGACACTT ACCGACACGT CGCGACACTC GGGGACACTG
TGTGACACTT TTGTACACGT AATTACACAC GTTTACACGG
GTAACCACCG CGGACCACCT ATGACCACCA TTGACCACAG
GTTACCACAT CCACCCACGA CTACCCACTC ACCCCACGC
CGCCCCACTT ATCCCCACTA TGTCCCACTC AGGGCCACCC
CATGCCACGG GAATCCACTT TCATCCACCT GCGTCCACAT
ACTTCCACCA TCTTCCACAG GGAAGCACTA GCCAGCACGT
AGGAGCACTG AGCCGCACCG TGCCGCACAA TAGCGCACGT
GATCGCACGG ATTCGCACAC GCAGGCACGA GTAGGCACTC
GGCGGCACTT ACGGGCACGG TTCTGCACGG CAGTGCACCA
CACATCACAT CGGATCACGA ATGATCACGT TATATCACAC
CCACTCACCT CCTCTCACAG CAAGTCACAA AACGTCACAC
GTCGTCACGG CCGGTCACTA CTGGTCACGC TCATTCACGA
TTATTCACTC TGCTTCACTT ACTTTCACGT CGTTTCACTC
TCAAAGACAC CCCAAGACCG TAGAAGACTC GCGAAGACCC
CAACAGACAG TACCAGACCC GCCCAGACTC GTCCAGACGA
CCGCAGACTG CATCAGACCT CCTGAGACAA AAATAGACGT
GGCTAGACAG CGGTAGACAC TATTAGACGA GTTTAGACCC
AAAACGACAG TAAACGACCA GCAACGACTA GTAACGACGC
GGCACGACGT GAGACGACAA ACGACGACTG AATACGACCT
ACCCCGACCG TCCCCGACAA GGAGCGACGA TACGCGACCT
GCCGCGACTT AGGGCGACGG CATGCGACCC ATTTCGACTG
CCGAGGACCT CATAGGACTG CGACGGACGA ATACGGACGT
CCCCGGACTT AGCCGGACGC GATCGGACCC TCTCGGACTC
TTTCGGACGA ACGGGGACCC TGATGGACCT CTATGGACAG
GACTGGACGA TTCTGGACCC GGGTGGACAT AGTTGGACCA
TGTTGGACAG CTTTGGACCT TAAATGACGT GGCATGACCA
AATATGACGA AGACTGACTG GGGCTGACTA GGAGTGACCT
TACGTGACGA GTCGTGACCC TGGGTGACAT CTGGTGACCG
GGTGTGACAG ACATTGACAC CCCTTGACAA AAGTTGACTC
CGAAATACCA ATAAATACCT AGCAATACCC GATAATACGC
ATTAATACAG TTTAATACCA CCGCATACGT AGGCATACTC
CTAGATACCC CGCGATACCT ATCGATACCA TTCGATACAG
TGTGATACCC AAATATACTG GCATATACAA GAGTATACTA
ACGTATACAG TCGTATACCA GGCACTACTG ACGACTACGT
CGGACTACTC AGACCTACCA TGACCTACAG CTACCTACCT
CGCCCTACCC GGGCCTACCG TGTCCTACCT CTTCCTACAG
GCCGCTACGG CCGGCTACGC AGGGCTACTT CTGGCTACTA
```

-continued

```
GAATCTACCC TCATCTACTC TTATCTACGA TAGTCTACAC
CGTTCTACGA ATTTCTACGT TACAGTACGG GTCAGTACCA
CATAGTACGT ATACGTACTG CCCCGTACGG GCGCGTACGC
GTGCGTACTA GTAGGTACCT GGCGGTACCC CGGGGTACCG
TTGGGTACAT AATGGTACGC GTTGGTACAG ACCTGTACAT
TAAATTACTG GCAATTACCG ACGATTACCA TCGATTACAG
GCTATTACAT CCACTTACTC AGACTTACGT CTACTTACGA
GACCTTACAG ACCCTTACTA ATCCTTACGC CAGCTTACAC
TGTCTTACGA CGATTTACAG TTATTTACCT TGCTTTACCC
GTGTTTACAT CGTTTTACCT ATTTTTACCA TTTTTTACAG
CCAAAACCGC AGAAAACCTT CTAAAACCTA ACCAAACCGA
ATCAAACCTC TGTAAACCTA TAACAACCGG ATGCAACCCC
ACAGAACCGT CGAGAACCTC AGCGAACCTA CTCGAACCTT
TCTGAACCGA TTTGAACCTG TGGTAACCGC CATTAACCAA
GTCACACCCG CTGACACCCC GGTACACCAC ACACCACCGC
CGACCACCTT ATACCACCTA CCCCCACCGA CTCCCACCTC
GTGCCACCTG TTTCCACCTT CGGGCACCCA ATGGCACCCT
GTTGCACCAA GACTCACCTT CCTCACCCT CCTTCACCCC
GCAAGACCGT GGCAGACCTA AGACGACCCG TGACGACCAA
GGGCGACCCA AGTCGACCAT CTTCGACCAA GGAGGACCTT
GCCGGACCGA GTCGGACCTC CTGGGACCTG TTATGACCGG
AAGTGACCCC CGTTGACCGG CAAATACCAT CCGATACCTT
AGGATACCGC CATATACCCG CCCCTACCCT GATCTACCTC
TCTCTACCCC AAAGTACCAC GTAGTACCGG CACGTACCAA
ACGGTACCTC CGGGTACCGT ATGGTACCGA TGATTACCTT
TCCTTACCGA TTCTTACCTC AGTTTACCTA CTTTTACCTT
TTCAACCCTG AAACACCCGC GTACACCCAG CACCACCCGA
CGGCACCCAT ATGCACCCAA TTGCACCCCG GTTCACCCCT
ATTGACCCTG GGATACCCGA TACTACCCCT GCCTACCCTT
AGGTACCCGG CATTACCCCC CAAACCCGC AACACCCCGA
AGGACCCCAT CTGACCCCAA GGTACCCCA TCACCCCGG
AAAGCCCCGT GGCGCCCCAG CGGGCCCCAC TATGCCCCGA
GTTGCCCCCC CCTTCCCCAA TTGAGCCCTT GTTAGCCCTG
TGACGCCCCC CGCCGCCCAG TTCCGCCCCT GGGCGCCCAC
CTTCGCCCCC GAATGCCCAG ACATGCCCTA ATATGCCCGC
CCCTGCCCTC AGCTGCCCGT CTCTGCCCGA AAGTGCCCAA
TAGTGCCCCG GCGTGCCCTG GATTGCCCCT TCTTGCCCTT
AACATCCCCT TGGATCCCGG GGTATCCCGT ACACTCCCAT
AAGCTCCCTT ACTCTCCCCG TCTCTCCCAA AAAGTCCCCA
TAAGTCCCAG CACGTCCCCC GAGGTCCCCG TCGGTCCCTG
TATGTCCCCT GCTGTCCCTT CCATTCCCGG ATCTTCCCTG
GACAAGCCTA ACCAAGCCAG TCCAAGCCCA AAACAGCCCG
TAACAGCCAA GAGCAGCCCA TCGCAGCCTA TTGCAGCCGC
AATCAGCCAT GAAGAGCCTT TCAGAGCCCT GCGGAGCCAT
ACTGAGCCCA TCTGAGCCAG AGGTAGCCCC CATTAGCCGG
CAAACGCCCG TACACGCCAC CATACGCCAT GAACCGCCTC
TCACCGCCCC CCCCCGCCAG GCGCCGCCAC TTGGCGCCGT
AATGCGCCAC GTTGCGCCGG AGATCGCCTA CTATCGCCTT
ACCTCGCCGT CGCTCGCCTC GGGTCGCCTG TGTTCGCCTT
AAAAGGCCTT ACGAGGCCAT TATAGGCCTA GCTAGGCCCA
TGACGGCCGG CTTCGGCCAA CAAGGGCCTC AACGGGCCTA
GCCGGGCCAG CCGGGGCCAC ATATGGCCCG TTATGGCCAA
TAGTGGCCGC GTGTGGCCCA CGTTGGCCAA ATTTGGCCAT
GGAATGCCAC GTCATGCCAT TGGATGCCCC TTACTGCCTT
TGCCTGCCTC ACTCTGCCGC CGTCTGCCTT ATTCTGCCTA
GTAGTGCCAA CACGTGCCGG GAGGTGCCGC ATGGTGCCAG
TTGGTGCCCA CCATTGCCCC ACCTTGCCCA TCCTTGCCAG
AGAAATCCAA TGAAATCCCG CTAAATCCAT CGCAATCCAC
GGGAATCCAG TGTAATCCAT CTTAATCCCG GCTCATCCGA
GTTCATCCTC GAAGATCCGG ATAGATCCAC AGCGATCCAT
CTCGATCCAA AAGGATCCGA TACTATCCTC GCCTATCCCC
CCGTATCCCG CATTATCCTT CGACCTCCAA ATACCTCCAT
AGCCCTCCAC ATTCCTCCCG TTTCCTCCAA TTGGCTCCTG
GTTGCTCCTT CTATCTCCGG GACTCTCCAA ACCTCTCCTG
GGGTCTCCGT TGTTCTCCGG AAAAGTCCGG GTAAGTCCAC
GGCAGTCCAT GAGAGTCCGA TTGAGTCCCC TGACGTCCTT
TCCCGTCCGA TTCCGTCCTC AGTCGTCCTA CTTCGTCCTT
GGAGGTCCAA AGGGGTCCAG TGGGGTCCCA CCCTGTCCCT
GATTGTCCTC TCTTGTCCCC CAAATTCCTA AACATTCCTC
CCGATTCCAA TTACTTCCGG AAGCTTCCCC CGTCTTCCGG
CACGTTCCTT TATGTTCCTC GCTGTTCCCC AGATTTCCCG
TGATTTCCAA GGGTTTCCCA AGTTTTCCAT CTTTTTCCAA
TAAAAAGCTC GCAAAAGCCC TCGAAAGCAC CCACAAGCTG
GACCAAGCAC ATCCAAGCGG CAGCAAGCAG CATGAAGCTA
CGATAAGCAC AGCTAAGCAA TGCTAAGCCG CTCTAAGCAT
AAGTAAGCGT TTTTAAGCAC GAAACAGCAA ACAACAGCTG
CTCACAGCGG AAGACAGCAG TAGACAGCCA GCGACAGCTA
GTGACAGCGC TACCCAGCTA GCCCCAGCCA AGAGCAGCGG
GACGCAGCAT GGGGCAGCGA GCTTCAGCGC GTTTCAGCTA
CCAAGAGCCT CCTAGAGCAG CACCGAGCAT CGGCGAGCGA
ATGCGAGCGT TATCGAGCAC ACAGGAGCCC CCCGGAGCCA
```

-continued

GGATGAGCAT AACTGAGCGG GTCTGAGCAC TGGTGAGCCT
CTGTGAGCAG GGTTGAGCCG AGCATAGCCG TGCATAGCAA
TAGATAGCGT GATATAGCGG ATTATAGCAC GGACTAGCTA

GCCCTAGCGT AGGCTAGCTG TGAGTAGCAT CTAGTAGCCG

TTCGTAGCAC GGGGTAGCCT AGTGTAGCAA TGTGTAGCCG
CTTGTAGCAT AAATTAGCTC CACTTAGCTA ACGTTAGCAC
AAAAACGCTG GCAAACGCAA GAGAACGCTA ACGAACGCAG
TCGAACGCCA TGACACGCGT GACCACGCCA TCCCACGCTA
TTCCACGCGC AGTCACGCGA CTTCACGCGT GCCGACGCAT
CGATACGCCA ATATACGCCT AGCTACGCCC GATTACGCGC
ATTTACGCAG TTTTACGCCA GAAACCGCCC TCAACCGCTC
TTAACCGCGA TAGACCGCAC CGTACCGCGA ATTACCGCGT

CAACCCGCTG GCCCCCGCAC CCGCCCGCAG TGAGCCGCGC

TTCGCCGCGT CCTGCCGCTA CTTGCCGCGC GGCTCCGCTG
ACGTCCGCGT CGGTCCGCTC ACCAGCGCAT AAACGCGCCT
AATCGCGCAG TATCGCGCCA GCTCGCGCTA GTTCGCGCGC

GAAGGCGCTG ACAGGCGCAA TCAGGCGCCG CCCGGCGCAC

AAGGGCGCTA GCGGGCGCAG TCTGGCGCAT TACTGCGCGC

GTCTGCGCCA CATTGCGCGT CGAATCGCAG TTAATCGCCT

TGCATCGCCC GTGATCGCAT CGTATCGCCT ATTATCGCCA

TTTATCGCAG TGGCTCGCTC GACGTCGCGC ATCGTCGCAG

TTCGTCGCCA CAGGTCGCGG AGTGTCGCCC TAATTCGCTG

GCATTCGCCG ACGTTCGCCA TCGTTCGCAG GCTTTCGCAT

TTGAAGGCTG GTTAAGGCTT CTACAGGCAC CGCCAGGCAT

ATCCAGGCAA TTCCAGGCCG CAGCAGGCGA TGTCAGGCAC

GAATAGGCAT AGCTAGGCGG TAGTAGGCCT GCGTAGGCTT

GATTAGGCCG TCTTAGGCTG GAAACGGCGG ATAACGGCAC

AGCACGGCAT CTCACGGCAA AAGACGGCGA GGTCCGGCTA

AGAGCGGCAA TGAGCGGCCG CTAGCGGCAT CGCGCGGCAC

GGGGCGGCAG TGTGCGGCAT CTTGCGGCCG AATTCGGCTC

TGAAGGGCTC TTCAGGGCTT CCTAGGGCGA CTTAGGGCTC

GTACGGGCAT GGCCGGGCAC CGGCGGGCAG TTGCGGGCCT

GTTCGGGCCG TCAGGGGCGC TTAGGGGCTA CGTGGGGCTA

ATTGGGGCTT CAATGGGCAC AACTGGGCAA TACTGGGCCG

GCCTGGGCTG CCGTGGGCTC AGGTGGGCGT CTGTGGGCGA

TGCATGGCGG AAGATGGCCT GATATGGCAA ACTATGGCTG

AACCTGGCTT GACGTGGCCG TCCGTGGCTG CAGGTGGCCC

AGTGTGGCGG GCATTGGCGC GTATTGGCTA ATGTTGGCTG

TTGAATGCGT AATAATGCAC GTTAATGCGG CCTCATGCCA

CAAGATGCCG TACGATGCAC CATGATGCAT ACATATGCGA

ATATATGCTC CCCTATGCGC AGCTATGCTT CTCTATGCTA

-continued

GCGTATGCGG TCTTATGCGT GAAACTGCTT TCAACTGCCT

GCGACTGCAT ACTACTGCCA TCTACTGCAG TACCCTGCAT

TGGCCTGCGA CATCCTGCAC GACGCTGCTA ACCGCTGCAG

TCCGCTGCCA GTATCTGCCG CGGTCTGCCT ATGTCTGCCA

TTGTCTGCAG GTTTCTGCAT TTCAGTGCGG CAGAGTGCCA

AAACGTGCTC CACCGTGCTA ACGCGTGCAC GATGGTGCAC

ATTGGTGCGG GGATGTGCTA GCCTGTGCGT AGGTGTGCTG

TCAATTGCGA TTAATTGCTC TGCATTGCTT ACTATTGCGT

CGTATTGCTC GGACTTGCAT AACCTTGCGG GTCCTTGCAC

TGGCTTGCCT CTGCTTGCAG GGTCTTGCCG TGAGTTGCTA

TCCGTTGCGT CCTGTTGCGC AGTGTTGCTT CTTGTTGCTA

CACTTTGCAT CGGTTTGCGA ATGTTTGCGT TATTTTGCAC

GAAAAATCGC ATAAAATCAG TTAAAATCCA GTGAAATCAA

CGTAAATCCA ATTAAATCCT TGAGAATCCC CGCGAATCAG

TTCGAATCCT GGGGAATCAC CTTGAATCCC ACGTAATCCT

AATTAATCTG GCTTAATCAA TCGACATCGA TTGACATCTC

TGACCATCCT CTACCATCAG GACCCATCGA TTCCCATCCC

GGGCCATCAT AGTCCATCCA TGTCCATCAG CTTCCATCCT

TGGGCATCTA CGATCATCGA ATATCATCGT CCCTCATCTT

AGCTCATCGC GATTCATCCC TCTTCATCTC TTTTCATCGA

CAAAGATCGT AGGAGATCAC ATTCGATCTG AAAGGATCGC

GTAGGATCAG CACGGATCGA CGGGGATCAT ATGGGATCAA

TTGGGATCCG GTTGGATCCT ACCTGATCCG TCCTGATCAA

GCAATATCAT GAGATATCTT TCGATATCCT TATATATCTG

GCTATATCCG TGACTATCGA GACCTATCCT TCCCTATCTT

CCTCTATCTC AGTCTATCGT CTTCTATCGA AACGTATCTG

GCCGTATCAA CGATTATCCT ATATTATCCA TTATTATCAG

CTCTTATCCC GTGTTATCCG CGTTTATCAG TTTTTATCCT

TTAAACTCAC TGCAACTCAT CTCAACTCCG TAGAACTCGA

GTGAACTCCC CGTAACTCAC GGACACTCTT GCCCACTCGA

GTCCACTCTC CTGCACTCTG AGAGACTCCG TGAGACTCAA

GGGGACTCCA AGTGACTCAT CTTGACTCAA CACTACTCTT

TATTACTCTC GCTTACTCCC GCAACCTCGC GTAACCTCTA

ATGACCTCTG ATCCCCTCCG TTCCCCTCAA AGTCCCTCAC

GGAGCCTCTC GTCGCCTCTT TGCTCCTCGG AAGTCCTCCT

GATTCCTCAA ACTTCCTCTG GGAAGCTCCG AGGAGCTCCA

TGGAGCTCAG CTGAGCTCCT GGTAGCTCAT ACACGCTCGT

CGACGCTCTC AGCCGCTCTA CTCCGCTCTT TCTCGCTCGA

TTTCGCTCTC TAAGGCTCGG ATGGGCTCCC CCATGCTCAG

GACTGCTCTC TCCTGCTCCC CAGTGCTCTG CCTTGCTCCT

-continued

AATATCTCTC CGCCTCTCGG GGGCTCTCGC TACGTCTCTC
GCCGTCTCCC CCGGTCTCCG CATGTCTCTT GAATTCTCGG
ATATTCTCAC AGCTTCTCAT CTCTTCTCAA AAGTTCTCGA
ACAAAGTCTC CGAAAGTCGT ATAAAGTCGA CCCAAGTCTA
CTCAAGTCGC AAGAAGTCAC GTGAAGTCGG TTTAAGTCGT
CCGCAGTCCA CCAGAGTCTT AGAGAGTCGC CGCGAGTCGA
ATCGAGTCGT CAGGAGTCAT TCGTAGTCGT GCTTAGTCGG
TAAACGTCTG GCAACGTCCG ACGACGTCCA TCGACGTCAG
GCTACGTCAT CCACCGTCTC AGACCGTCGT CTACCGTCGA
GACCCGTCAG ACCCCGTCTA ATCCCGTCGC CAGCCGTCAC
TGTCCGTCGA CGATCGTCAG TTATCGTCCT TGCTCGTCCC
GTGTCGTCAT CGTTCGTCCT ATTTCGTCCA TTTTCGTCAG
GGAAGGTCGC GTCAGGTCGT CATAGGTCCA ACTCGGTCAC
TAAGGGTCCC GCAGGGTCTC GTAGGGTCGA CACGGGTCAG
GAGGGGTCAC ATGGGGTCGG TCCTGGTCGG AGTTGGTCTG
GGCATGTCTG ACGATGTCGT CGGATGTCTC AGACTGTCCA
TGACTGTCAG CTACTGTCCT CGCCTGTCCC GGGCTGTCCG
TGTCTGTCCT CTTCTGTCAG GCCGTGTCGG CCGGTGTCGC
AGGGTGTCTT CTGGTGTCTA GAATTGTCCC TCATTGTCTC
TTATTGTCGA TAGTTGTCAC CGTTTGTCGA ATTTTGTCGT
CGAAATTCTG GTGAATTCTT TTTAATTCTG GGACATTCCC
GTCCATTCCT TGGCATTCAC CATCATTCGA CCAGATTCGG
ATCGATTCTG AAATATTCCA TAATATTCAG CACTATTCCC
GAGTATTCCG TCGTATTCTG TATTATTCCT GCTTATTCTT
TAAACTTCGT GGCACTTCCA AATACTTCGA AGACCTTCTG
GGGCCTTCTA GGAGCTTCCT TACGCTTCGA GTCGCTTCCC
TGGGCTTCAT CTGGCTTCCG GGTGCTTCAG ACATCTTCAC
CCCTCTTCAA AAGTCTTCTC GTCAGTTCTG CCGAGTTCGA
CTGAGTTCTC CGACGTTCCT ATACGTTCCA TTACGTTCAG
CTCCGTTCCC GTGCGTTCCG CGTCGTTCAG TTTCGTTCCT
CGGGGTTCTA ATGGGTTCTT TGATGTTCGA GACTGTTCCT
TCCTGTTCTT CCTTGTTCTC AGTTGTTCGT CTTTGTTCGA
AAAATTTCAG TAAATTTCCA GCAATTTCTA GTAATTTCGC
GGCATTTCGT GAGATTTCAA ACGATTTCTG AATATTTCCT
ACCCTTTCCG TCCCTTTCAA GGAGTTTCGA TACGTTTCCT
GCCGTTTCTT AGGGTTTCGG CATGTTTCCC ATTTTTTCTG
TGAAAAAGGA GACAAAAGCT TCCAAAAGTT CCTAAAAGTC
AGTAAAAGGT CTTAAAAGGA GCACAAAGAT GAGCAAAGTT
TCGCAAAGCT TATCAAAGTG GCTCAAAGCG GAAGAAAGCA
TCAGAAAGTA TTAGAAAGGC TGCGAAAGGT AAGGAAAGCG
TAGGAAAGAA ACTGAAAGTT CGTGAAAGGC GTCTAAAGTG

-continued

CCGTAAAGGA CTGTAAAGTC TTACCAAGGT TGCCCAAGGC
ACTCCAAGTC CGTCCAAGGT ATTCCAAGGA GCAGCAAGAC
CACGCAAGTG GAGGCAAGTC TCGGCAAGCC AGATCAAGCT
CTATCAAGCA ATCTCAAGCC AGTTCAAGAG TGTTCAAGCA
AAAAGAAGCA TAAAGAAGAG CACAGAAGCC GAGAGAAGCG
TCGAGAAGTG TATAGAAGCT GCTAGAAGTT CCACGAAGAC
GACCGAAGTG ACCCGAAGAA TCCCGAAGCG CAGCGAAGTC
AACGGAAGCT TGGGGAAGGG GGTGGAAGGT CGATGAAGTG
GTGTGAAGTT TTTTGAAGTG GAACTAAGGC ATACTAAGAG
TTACTAAGCA GTGCTAAGAA CGTCTAAGCA ATTCTAAGCT
TTGGTAAGTT GTTGTAAGTG AGATTAAGGA CTATTAAGGT
ACCTTAAGTT CGCTTAAGGC GGGTTAAGGG TGTTTAAGGT
CGCAACAGGG GGGAACAGGC AATCACAGTC GAAGACAGAC
ATAGACAGGG CCCGACAGTG TAGGACAGCC GCGGACAGTC
GTGGACAGGA GGTTACAGTA TACACCAGTT GCCACCAGCT
CATACCAGTC GAACCCAGAT AGCCCCAGGG TAGCCCAGCT
GCGCCCAGTT GATCCCAGCG TCTCCCAGTG TAAGCCAGTA
GCAGCCAGCA ACGGCCAGCG TCGGCCAGAA AATGCCAGTT
CTATCCAGAC CGCTCCAGAT ATCTCCAGAA TTCTCCAGCG
CAGTCCAGGA TGTTCCAGAC AAAAGCAGAC GTAAGCAGGG
CACAGCAGAA ACGAGCAGTC CGGAGCAGGT ATGAGCAGGA
CCACGCAGCA ACCCGCAGCC CAAGGCAGAT CCGGGCAGTT
AGGGGCAGGC CATGGCAGCG TCATGCAGGT TGCTGCAGTA
ACTTGCAGGA ATTTGCAGTC GGAATCAGTT GCCATCAGGA
GTCATCAGTC CTGATCAGTG TTACTCAGAC TGCCTCAGAT
CTCCTCAGCG TAGCTCAGGA GTGCTCAGCC CGTCTCAGAC
GCAGTCAGGT GGCGTCAGTA CAGTTCAGCT CCTTTCAGTG
AGAAAGAGCA TGAAAGAGAG CTAAAGAGCT CGCAAGAGCC
GGGAAGAGCG TGTAAGAGCT CTTAAGAGAG GGCCAGAGTG
ACGCAGAGGT CGGCAGAGTC ATAGAGAGCC AGCGAGAGCT
CTCGAGAGCA TAGGAGAGGG GATGAGAGGT CAATAGAGTG
GCCTAGAGAC CCGTAGAGAG CCGACGAGGT AGGACGAGTC
CGACCGAGCA ATACCGAGCT AGCCCGAGCC GATCCGAGGC
ATTCCGAGAG TTTCCGAGCA GTAGCGAGTG ACGGCGAGGC
CGGGCGAGTT ATGGCGAGTA TGATCGAGGT GACTCGAGCA
TCCTCGAGTA TTCTCGAGGC AGTTCGAGGA CTTTCGAGGT
TAAAGGAGGA GTAAGGAGCC GGCAGGAGCT TTGAGGAGAC
AATAGGAGGT CTACGGAGTG ACCCGGAGGG GGGCGGAGTT
TGTCGGAGTG GGAGGGAGCA TACGGGAGGT AGGGGGAGCG
TGGGGGAGAA CATGGGAGGC CCCTGGAGAT TCTTGGAGAC

-continued

```
CCGATGAGCA ACACTGAGTC CGACTGAGGT ATACTGAGGA
CCCCTGAGTA CTCCTGAGGC AAGCTGAGAC GTGCTGAGGG
TTTCTGAGGT GCTGTGAGAC AGATTGAGAG TGATTGAGCA
GACTTGAGGT GGGTTGAGAA AGTTTGAGCT CTTTTGAGCA
ACCAATAGCG TCCAATAGAA AAACATAGAG TAACATAGCA
GCACATAGTA GTACATAGGC GGCCATAGGT GAGCATAGAA
ACGCATAGTG AATCATAGCT TCAGATAGAT TAGGATAGTT
GCGGATAGCT GATGATAGTG ACTGATAGAA TCTGATAGCG
CAATATAGGT AGGTATAGAC CAAACTAGAG TACACTAGCC
GCCACTAGTC GTCACTAGGA CCGACTAGTG CATACTAGCT
TCACCTAGAC CCCCCTAGCG TAGCCTAGTC GCGCCTAGCC
GTAGCTAGGT GGCGCTAGGC CGGGCTAGGG AATGCTAGCC
TGATCTAGTG CTTTCTAGTG ACGAGTAGCT AATAGTAGTG
GCTAGTAGAA AGACGTAGGA CTACGTAGGT ACCCGTAGTT
CGCCGTAGGC GGGCGTAGGG TGTCGTAGGT TACGGTAGTG
GCCGGTAGCG CCGGGTAGCC GAATGTAGGC ATATGTAGAG
TTATGTAGCA GTGTGTAGAA CGTTGTAGCA ATTTGTAGCT
GGAATTAGCC GTCATTAGCT TGGATTAGAC CATATTAGGA
CGACTTAGTG GTGCTTAGTT TTTCTTAGTG TAAGTTAGGC
GTAGTTAGCA ATGGTTAGCG TTGGTTAGAA CCATTTAGAC
GACTTTAGTG ACCTTTAGAA TCCTTTAGCG CAGTTTAGTC
CGAAAACGGG GTGAAACGGT TTTAAACGGG CATCAACGTA
CCAGAACGTG GACGAACGAC ATCGAACGGG CAGGAACGAG
TCGTAACGGG GCTTAACGGT TAAACACGTT GCAACACGCT
TCGACACGAT AATACACGTA GCTACACGAG AGACCACGGG
GACCCACGAT GGGCCACGGA TACGCACGTA GCCGCACGCA
CGATCACGAT ATATCACGAA TTATCACGCG CTCTCACGAC
AAGTCACGGC GTGTCACGAG CGTTCACGCG TTTTCACGAT
CAAAGACGAA AACAGACGAC GTCAGACGGG CCGAGACGTA
CTGAGACGGC ACACGACGCC CCCCGACGCA CACGGACGAT
CGGGGACGGA ATGGGACGGT TATGGACGAC TGATGACGTA
TCCTGACGGT CCTTGACGGC AGTTGACGTT CTTTGACGTA
GCAATACGGA GTAATACGTC GGCATACGTT ACGATACGGG
TGACTACGAT CTACTACGCG TTCCTACGAC GGGCTACGCT
AGTCTACGAA TGTCTACGCG CTTCTACGAT GGAGTACGTA
GCCGTACGGT AGGGTACGTG GATTTACGAC ATTTTACGGG
GAAAACCGCT TCAAACCGTT TGCAACCGGA TAGAACCGAT
GATAACCGAG ACTAACCGTA ATTAACCGGC GCCCACCGAT
TGAGACCGGT GACGACCGCA TCCGACCGTA TTCGACCGGC
AGTGACCGGA CTTGACCGGT GTATACCGTG ACGTACCGGC
CGGTACCGTT ATGTACCGTA TGACCCCGGC TTCCCCCGGT
```

-continued

```
CCTCCCCGTA CTTCCCCGGC CAAGCCCGTG GCCGCCCGAC
CCGGCCCGAG ATATCCCGCC AGCTCCCGCT CTCTCCCGCA
TAGTCCCGGG GATTCCCGGT CAAAGCCGCC AACAGCCGCA
TACAGCCGAG GGTAGCCGGA GAACGCCGTG ACACGCCGAA
TCACGCCGCG CCCCGCCGAC AAGCGCCGTA GCGCGCCGAG
TCTCGCCGAT AAAGGCCGCT AATGGCCGAG TATGGCCGCA
GCTGGCCGTA GTTGGCCGGC CGCTGCCGTG GGGTGCCGTC
TCGATCCGGC TTGATCCGTA GACCTCCGGC ATCCTCCGAG
TTCCTCCGCA CAGCTCCGGG AGTCTCCGCC TGGGTCCGTC
ACATTCCGTT CGATTCCGGC AGCTTCCGGA CTCTTCCGGT
AAGTTCCGAT GATTTCCGCA TCTTTCCGTA TTTTTCCGGC
CGAAAGCGAA ATAAAGCGAT AGCAAGCGAC ATTAAGCGCG
TTTAAGCGAA CTAGAGCGAC CGCGAGCGAT ATCGAGCGAA
TTCGAGCGCG CAGGAGCGGA TGTGAGCGAC TAATAGCGTA
GCATAGCGCA ACGTAGCGCG TCGTAGCGAA AATTAGCGTT
GCTACGCGGA GTTACGCGTC AGACCGCGAA TGACCGCGCG
CTACCGCGAT CGCCCGCGAC GGGCCGCGAG TGTCCGCGAT
CTTCCGCGCG GGTGCGCGTA GAATCGCGAC ATATCGCGGG
CCCTCGCGTG TAGTCGCGCC GCGTCGCGTC GTGTCGCGGA
CAAAGGCGGG GTCAGGCGAA TCACGGCGGC TTACGGCGTA
CGTCGGCGTA ATTCGGCGTT GTAGGGCGAT GGCGGGCGAC
CGGGGGCGAG TTGGGGCGCT GTTGGGCGCG ACCTGGCGCT
AAAATGCGTA GCAATGCGAG CACATGCGTC GAGATGCGTG
ACGATGCGAA TCGATGCGCG TATATGCGTT GCTATGCGCT
GACCTGCGCG TCCCTGCGTG CAGCTGCGCC AGTCTGCGGG
AACGTGCGTT CGATTGCGCG TTATTGCGAT TGCTTGCGAC
GTGTTGCGCT CGTTTGCGAT ATTTTGCGAA TTTTTGCGCG
GAAAATCGTC TCAAATCGCC CCCAATCGAG GCGAATCGAC
CAACATCGCG TACCATCGAC CATCATCGAT CCTGATCGCA
GGCTATCGCG CGGTATCGCC AATTATCGGG GTTTATCGAC
AAAACTCGCG TAAACTCGAA GAGACTCGCA TCGACTCGTA
TTGACTCGGC AATACTCGAT GACCCTCGTA ACCCCTCGAG
TCCCCTCGCA TACGCTCGAT TGGGCTCGGA CATGCTCGAC
CGATCTCGTA ATATCTCGTT CCCTCTCGGT AGCTCTCGTC
TCTTCTCGGC TTTTCTCGTA CAAAGTCGTT CCGAGTCGAT
GATCGTCGAC ATTCGTCGGG AAAGGTCGTC CACGGTCGTA
ACGGGTCGAC TGATGTCGAT CTATGTCGCG TTCTGTCGAC
GGGTGTCGCT AGTTGTCGAA TGTTGTCGCG CTTTGTCGAT
GGCATTCGAA GAGATTCGGT TATATTCGGG TGACTTCGTA
TCCCTTCGGT CCTCTTCGGC AGTCTTCGTT CTTCTTCGTA
```

-continued

```
GGAGTTCGAT AACGTTCGGG GTCGTTCGAC TGGGTTCGCT
CTGGTTCGAG GGTGTTCGCG ACATTTCGCC CCCTTTCGCA
GGAAAAGGCG AGGAAAGGCA TGGAAAGGAG CTGAAAGGCT
GGTAAAGGAT ACACAAGGGT CGACAAGGTC AGCCAAGGTA
CTCCAAGGTT TCTCAAGGGA TTTCAAGGTC TAAGAAGGGG
ATGGAAGGCC CCATAAGGAG GACTAAGGTC TCCTAAGGCC
CAGTAAGGTG CCTTAAGGCT CCAACAGGGT AGAACAGGTC
CGCACAGGTA ATCACAGGTT CGGCCAGGCA ATGCCAGGCT
GTTCCAGGAA ACAGCAGGGC CGAGCAGGTT ATAGCAGGTA
CCCGCAGGGA CTCGCAGGTC GTGGCAGGTG TTTGCAGGTT
AACTCAGGCG TACTCAGGAA TGGTCAGGGT GGTTCAGGGG
TTAAGAGGAC TGCAGAGGAT CTCAGAGGCG TAGAGAGGGA
GTGAGAGGCC CGTAGAGGAC GGACGAGGTT GCCCGAGGGA
GTCCGAGGTC CTGCGAGGTG AGAGGAGGCG TGAGGAGGAA
GGGGGAGGCA AGTGGAGGAT CTTGGAGGAA CACTGAGGTT
TATTGAGGTC GCTTGAGGCC CCAATAGGCA ACCATAGGCC
AAACTAGGAC GTACTAGGGG CACCTAGGAA ACGCTAGGTC
CGGCTAGGGT ATGCTAGGGA CCCGTAGGCT GATGTAGGTC
TCTGTAGGCC GGATTAGGAA AGGTTAGGAG TGGTTAGGCA
CAAAACGGGT AGGAACGGAC ATTCACGGTG AAAGACGGGC
GTAGACGGAG CACGACGGGA CGGGACGGAT ATGGACGGAA
TTGGACGGCG GTTGACGGCT ACCTACGGCG TCCTACGGAA
TGAACCGGTG CTTACCGGTG AAACCCGGGT GGCCCCGGAG
CGGCCCGGAC TATCCCGGGA GTTCCCGGCC TCAGCCGGGG
CAATCCGGAG TACTCCGGCC GCCTCCGGTC GTCTCCGGGA
CCGTCCGGTG CATTCCGGCT GAAAGCGGGC ATAAGCGGAG
TTAAGCGGCA GTGAGCGGAA CGTAGCGGCA ATTAGCGGCT
TGAGGCGGCC CGCGGCGGAG TTCGGCGGCT GGGGGCGGAC
CTTGGCGGCC ACGTGCGGCT AATTGCGGTG GCTTGCGGAA
CCAATCGGAC GACATCGGTG ACCATCGGAA TCCATCGGCG
CAGATCGGTC AAACTCGGCA TAACTCGGAG CACCTCGGCC
GAGCTCGGCG TCGCTCGGTG TATCTCGGCT GCTCTCGGTT
ACAGTCGGAT AAGGTCGGTT ACTGTCGGCG TCTGTCGGAA
GGATTCGGCC GTCTTCGGCT TGGTTCGGAC CATTTCGGGA
TACAAGGGAT TGGAAGGGGA CATAAGGGAC GAACAGGGTT
TCACAGGGCT GCGCAGGGAT ACTCAGGGCA TCTCAGGGAG
AAAGAGGGCG TAAGAGGGAA GAGGAGGGCA TCGGAGGGTA
TTGGAGGGGC AATGAGGGAT CCATAGGGGA CTATAGGGTC
ACCTAGGGGC CGCTAGGGTT ATCTAGGGTA TGTTAGGGTC
CCTACGGGCA TTGCCGGGGT AATCCGGAC GTTCCGGGGG
GAAGCGGGTC TCAGCGGGCC CCCGCGGGAG GCGGCGGGAC
TACTCGGGGG AGGTCGGGCT CTGTCGGGCA GGTTCGGGAA
GAAAGGGGCG TCAAGGGGTG AAGAGGGGCA TAGAGGGGAG
GATAGGGGAT CAACGGGGTC AACCGGGGTA GCCCGGGGAG
CCGCGGGGAC TGAGGGGGGG CTTGGGGGGG GTATGGGGTT
GGCTGGGGTC CGGTGGGGTG TCCATGGGGC TTCATGGGTA
CCTATGGGGT AGTATGGGGT GTACTGGGAA CACCTGGGGG
GAGCTGGGGC ATGCTGGGAG TTGCTGGGCA TTAGTGGGTT
TGCGTGGGTC ACTGTGGGCG CGTGTGGGTT ATTGTGGGTA
GGATTGGGGG AACTTGGGAT AGGTTGGGGA CTGTTGGGGT
GGTAATGGTA GAACATGGGA TACATGGAC AGCCATGGAT
CTCCATGGAA AAGCATGGGA GCTGATGGGA GTTGATGGTC
CGCTATGGGG GGGTATGGGC CTAACTGGAC CGCACTGGAT
ATCACTGGAA TTCACTGGCG CAGACTGGGA TGTACTGGAC
TTGCCTGGTG GTTCCTGGTT CGAGCTGGAA ATAGCTGGAT
AGCGCTGGAC ATTGCTGGCG TTTGCTGGAA TACTCTGGTT
GCCTCTGGCT CATTCTGGTC TCAAGTGGGT TGCAGTGGTA
ACTAGTGGGA ATTAGTGGTC GGACGTGGAA AGGCGTGGAG
TGGCGTGGCA TGAGGTGGTT TCCGGTGGGA TTCGGTGGTC
AGTGGTGGTA CTTGGTGGTT AAATGTGGAC GTATGTGGGG
CACTGTGGAA ACGTGTGGTC CGGTGTGGGT ATGTGTGGGA
CAGATTGGCT CCTATTGGTG CACCTTGGTT TATCTTGGTC
GCTCTTGGCC TTAGTTGGGG AAGGTTGGCC CGTGTTGGGG
GGATTTGGTT GCCTTTGGGA GTCTTTGGTC CTGTTTGGTG
ACCAAATGAT AAACAATGCT AATCAATGAG TATCAATGCA
GCTCAATGTA GTTCAATGGC GAAGAATGTG ACAGAATGAA
TCAGAATGCG CCCGAATGAC AAGGAATGTA GCGGAATGAG
TCTGAATGAT TACTAATGGC GTCTAATGCA CATTAATGGT
CAAACATGCT CATACATGAG CCCCCATGAT TCTCCATGAC
AAAGCATGCC CACGCATGCA TTGGCATGGG GTTGCATGGT
CTATCATGTG ACCTCATGGG GGGTCATGTT TGTTCATGTG
AAAAGATGTG GCAAGATGAA GAGAGATGTA ACGAGATGAG
TCGAGATGCA TGACGATGGT GACCGATGCA TCCCGATGTA
TTCCGATGGC AGTCGATGGA CTTCGATGGT GCCGGATGAT
CGATGATGCA ATATGATGCT AGCTGATGCC GATTGATGGC
ATTTGATGAG TTTTGATGCA CAAATATGGA AACATATGGC
GTCATATGAG CTGATATGAC GGTATATGCC TTACTATGTG
CGTCTATGTG CACGTATGGT CGGGTATGAA ATGGTATGAT
TATGTATGGC GTTGTATGCA TCCTTATGAT CCTTTATGAC
CCAAACTGCT CCTAACTGAG CACCACTGAT CGGCACTGGA
ATGCACTGGT TATCACTGAC ACAGACTGCC CCCGACTGCA
```

-continued

```
GGATACTGAT AACTACTGGG GTCTACTGAC TGGTACTGCT
CTGTACTGAG GGTTACTGCG GGAACCTGGG AACACCTGAT
AGGACCTGGA CTGACCTGGT ACACCCTGCT GATCCCTGTA
ACTCCCTGAG TCTCCCTGCA AAAGCCTGAA TAAGCCTGCG
GCAGCCTGTG CACGCCTGAC GAGGCCTGAG ACGGCCTGTA
ATGGCCTGGC TATGCCTGAT TCCTCCTGGC TTCTCCTGTA
CCTTCCTGGT AGTTCCTGTC TAAAGCTGTC GCAAGCTGCC
TCGAGCTGAC CCACGCTGTG GACCGCTGAC ATCCGCTGGG
CAGCGCTGAG CATGGCTGTA CGATGCTGAC AGCTGCTGAA
TGCTGCTGCG CTCTGCTGAT AAGTGCTGGT TTTTGCTGAC
TACATCTGGG AGGATCTGCT CTGATCTGCA GGTATCTGAA
ACACTCTGGA ATACTCTGTC CCCCTCTGGC AGCCTCTGTT
CTCCTCTGTA GCGCTCTGGG TCTCTCTGGT GGCGTCTGCG
CGGGTCTGCC AATGTCTGGG GTTGTCTGAC CCTTTCTGCA
AGAAAGTGTG GGGAAGTGTA TAACAGTGGT GGCCAGTGCA
AATCAGTGGA ACAGAGTGGG CTCGAGTGTG GCGGAGTGGA
GTGGAGTGTC CAATAGTGCA AACTAGTGCC GGTTAGTGGC
GGAACGTGCC GTCACGTGCT TGGACGTGAC CATACGTGGA
CGACCGTGTG GTGCCGTGTT TTTCCGTGTG TAAGCGTGGC
GTAGCGTGCA ATGGCGTGCG TTGGCGTGAA CCATCGTGAC
GACTCGTGTG ACCTCGTGAA TCCTCGTGCG CAGTCGTGTC
GCAAGGTGGG ACGAGGTGGA ATGAGGTGTC AGACGGTGCT
CTACGGTGCA ATCCGGTGCC AGTCGGTGAG TGTCGGTGCA
GGAGGGTGTG AGGGGGTGTA CTGGGGTGTT TTATGGTGGT
TGCTGGTGGC ACTTGGTGTC CGTTGGTGGT ATTTGGTGGA
CAAATGTGAG TACATGTGCC GCCATGTGTC GTCATGTGGA
CCGATGTGTG CATATGTGCT TCACTGTGAC CCCCTGTGCG
TAGCTGTGTC GCGCTGTGCC GTAGTGTGGT GGCGTGTGGC
CGGGTGTGGG AATGTGTGCC TGATTGTGTG CTTTTGTGTG
CCAAATTGTC AGAAATTGGT CTAAATTGGA GACAATTGAG
ACCAATTGTA ATCAATTGGC CAGAATTGAC TGTAATTGGA
TAACATTGTG GCACATTGCG ACGCATTGCA TCGCATTGAG
GCTCATTGAT ACAGATTGTT CGAGATTGGC AGCGATTGGA
CTCGATTGGT AAGGATTGAT GATGATTGCA TCTGATTGTA
TTTGATTGGC TGGTATTGTC CCGACTTGCA ACACCTTGTC
CGACCTTGGT ATACCTTGGA CCCCCTTGTA CTCCCTTGGC
AAGCCTTGAC GTGCCTTGGG TTTCCTTGGT GCTGCTTGAC
AGATCTTGAG TGATCTTGCA GACTCTTGGT GGGTCTTGAA
AGTTCTTGCT CTTTCTTGCA TAAAGTTGCT GCAAGTTGTT
GGCAGTTGGA GAGAGTTGAT AATAGTTGCA TATAGTTGAG
TCCCGTTGAT CCTCGTTGAC GGAGGTTGGT AACGGTTGAG
TACGGTTGCA GCCGGTTGTA GTCGGTTGGC CTGGGTTGGG
TTATGTTGTG CGTTGTTGTG CCGATTTGGT AGGATTTGTC
CGACTTTGCA ATACTTTGCT AGCCTTTGCC GATCTTTGGC
ATTCTTTGAG TTTCTTTGCA GTAGTTTGTG ACGGTTTGGC
CGGGTTTGTT ATGGTTTGTA TGATTTTGGT GACTTTTGCA
TCCTTTTGTA TTCTTTTGGC AGTTTTTGGA CTTTTTTGGT
GATAAAATAC ATTAAAATGG CAACAAATTT CCGCAAATAT
TTCGAAATGG CAGGAAATCA GCATAAATGA GTATAAATTC
GGCTAAATTT ACGTAAATGG AAAACAATTT ACGACAATAT
TATACAATTA GCTACAATCA TGACCAATGG CTTCCAATGG
CAAGCAATTC AACGCAATTA GCCGCAATAG CCGGCAATAC
ATATCAATCG TTATCAATAA TAGTCAATGC GTGTCAATCA
CGTTCAATAA ATTTCAATAT CAAAGAATCG TACAGAATAC
CATAGAATAT GAACGAATTC TCACGAATCC CCCCGAATAG
GCGCGAATAC TTGGGAATGT AATGGAATAC GTTGGAATGG
AGATGAATTA CTATGAATTT ACCTGAATGT CGCTGAATTC
GGGTGAATTG TGTTGAATTT TCGATAATGG GCTATAATGT
AGACTAATAT CTACTAATAA GACCTAATGG ATCCTAATAC
CAGCTAATGC AGTCTAATCG TGTCTAATAA TGGGTAATTG
GGTGTAATTT CGATTAATGG GTGTTAATGT TTTTTAATGG
ACAAACATTT CGAAACATGC AGCAACATGA CTCAACATGT
AAGAACATAT GATAACATCA TCTAACATTA TTTAACATGC
CCAGACATTC AGAGACATGT CTAGACATGA GACGACATAG
ACCGACATTA ATCGACATGC CAGGACATAC TGTGACATGA
TCGTACATGC TTGTACATTA GCTACCATAC CCACCCATTT
AGACCCATGC CGCCCCATGA ATCCCCATGT CAGCCCATAT
CCGGCCATCA GAATCCATGA TTATCCATCC TGCTCCATCT
CTCTCCATAG AAGTCCATGG GTGTCCATAC CGTTCCATCC
GGAAGCATGT AACAGCATAG TACAGCATCA GCCAGCATTA
GTCAGCATGC CTGAGCATGG ACACGCATCG TCACGCATAA
TAGCGCATTA GCGCGCATCA ACTCGCATAT TAAGGCATCT
GCAGGCATTT GGCGGCATGA GAGGGCATAT AATGGCATCA
TATGGCATAG CCTTGCATGG GTAATCATTG ACGATCATGC
CGGATCATTT ATGATCATTA CTACTCATCC CGCCTCATCT
ATCCTCATCA TTCCTCATAG TGTCTCATCC CCGGTCATGT
AGGGTCATTC GAATTCATCT TCATTCATTT TGCTTCATGA
TAGTTCATAT GATTTCATAG ACTTTCATTA ATTTTCATGC
CGAAAGATCG TTAAAGATAT TGCAAGATAC GTGAAGATCT
CGTAAGATAT ATTAAGATAA TTTAAGATCG GGACAGATTC
GTCCAGATTT ATCGAGATCG TTCGAGATAA AGTGAGATAC
```

-continued

AAATAGATTA GCATAGATAG CACTAGATTC GAGTAGATTG
ACGTAGATAA TCGTAGATCG TATTAGATTT GCTTAGATCT
GCAACGATGT GGCACGATTA AGACCGATCG TGACCGATAA
GGGCCGATCA AGTCCGATAT CTTCCGATAA GGAGCGATTT
GCCGCGATGA GTCGCGATTC CTGGCGATTG TTATCGATGG

AAGTCGATCC CGTTCGATGG GTCAGGATCG CTGAGGATCC

GGTAGGATAC ACACGGATGC CGACGGATTT ATACGGATTA
CCCCGGATGA CTCCGGATTC GTGCGGATTG TTTCGGATTT
CGGGGGATCA ATGGGGATCT GTTGGGATAA GACTGGATTT
TCCTGGATCT CCTTGGATCC TAAATGATTA GCAATGATCA
ACGATGATCG TCGATGATAA AATATGATTT CTACTGATGG
GACCTGATAA ACCCTGATTG GGGCTGATGT TGTCTGATGG
TACGTGATTT GCCGTGATCT CATGTGATTC CGATTGATAA
ATATTGATAT AGCTTGATAC ATTTTGATCG TTTTTGATAA
ACAAATATCC CCCAATATCA CAACATATAA AACCATATAC
GTCCATATGG CCGCATATTA CTGCATATGC CCAGATATCT
CCTGATATAG GGCTATATAA GAGTATATGT TATTATATGG
AAAACTATAA TAAACTATCG GCAACTATTG CACACTATAC
GAGACTATAG ACGACTATTA ATGACTATGC TATACTATAT
CCACCTATCC ACCCCTATCA TCCCCTATAG GGAGCTATGG
AACGCTATAT AGGGCTATGA CTGGCTATGT TTATCTATTT
TGCTCTATTC ACTTCTATGC CGTTCTATTT ATTTCTATTA
CATAGTATTA CGACGTATGG GTGCGTATGT TTTCGTATGG
TAAGGTATTC GCAGGTATCC TCGGGTATAC AGATGTATAT
CTATGTATAA GACTGTATGG ATCTGTATAC CAGTGTATGC
AGTTGTATCG TGTTGTATAA GGCATTATCG CGGATTATCC
AATATTATGG GTTATTATAC AGACTTATTA CTACTTATTT
ACCCTTATGT CGCCTTATTC GGGCTTATTG TGTCTTATTT
TACGTTATGG AGGGTTATCT CTGGTTATCA GGTGTTATAA
GAATTTATTC TCATTTATCC CCCTTTATAG GCGTTTATAC
AGAAAACTGA CTAAAACTGT ACCAAACTTT CGCAAACTGC
GGGAAACTGG TGTAAACTGT ACGCAACTCT AATCAACTTG
GCTCAACTAA GAAGAACTAG ACAGAACTTA ATAGAACTGC
CCCGAACTTC AGCGAACTGT CTCGAACTGA AAGGAACTAA
TAGGAACTCG GCGGAACTTG GATGAACTCT TCTGAACTTT
CCGACACTCT CATACACTTG CGACCACTGA ATACCACTGT
CCCCCACTTT AGCCCACTGC GATCCACTCC TCTCCACTTC
TTTCCACTGA ACGGCACTCC TGATCACTCT CTATCACTAG
GACTCACTGA TTCTCACTCC GGGTCACTAT AGTTCACTCA
TGTTCACTAG CTTTCACTCT AAAAGACTAG TAAAGACTCA

GCAAGACTTA GTAAGACTGC GGCAGACTGT GAGAGACTAA

-continued

ACGAGACTTG AATAGACTCT ACCCGACTCG TCCCGACTAA

GGAGGACTGA TACGGACTCT GCCGGACTTT AGGGGACTGG

CATGGACTCC ATTTGACTTG GTCATACTTG CCGATACTGA

CTGATACTTC CGACTACTCT ATACTACTCA TTACTACTAG

CTCCTACTCC GTGCTACTCG CGTCTACTAG TTTCTACTCT

CGGGTACTTA ATGGTACTTT TGATTACTGA GACTTACTCT

TCCTTACTTT CCTTTACTTC AGTTTACTGT CTTTTACTGA

CAGAACCTCT CCTAACCTTG CACCACCTTT TATCACCTTC

GCTCACCTCC TTAGACCTGG AAGGACCTCC CGTGACCTGG

GGATACCTTT GCCTACCTGA GTCTACCTTC CTGTACCTTG

AACACCCTTT TGCCCCCTGG AAGCCCCTCT GATCCCCTAA

ACTCCCCTTG AAAGCCCTTA GCAGCCCTAG CACGCCCTTC

GAGGCCCTTG ACGGCCCTAA TCGGCCCTCG TATGCCCTTT

GCTGCCCTCT ATCTCCCTCG TTCTCCCTAA AGTTCCCTAC

TAAAGCCTAC CACAGCCTCG GAGAGCCTCC TCGAGCCTTC

TTGAGCCTGA CCACGCCTAG GACCGCCTTC TCCCGCCTCC

CAGCGCCTTG CCTCGCCTCT TGGGGCCTGC CATGGCCTAA

ACATGCCTGT CGATGCCTTC AGCTGCCTTA CTCTGCCTTT

TCTTGCCTGA TTTTGCCTTC GGTATCCTTA GAACTCCTGG

ATACTCCTAC AGCCTCCTAT CTCCTCCTAA AAGCTCCTGA

GCTGTCCTGA GTTGTCCTTC CGCTTCCTGG GGGTTCCTGC

AGAAAGCTAG TGAAAGCTCA GACAAGCTGT GGGAAGCTAA

AGTAAGCTCT CTTAAGCTCA TCGCAGCTGT GCTCAGCTGG

GAAGAGCTGA TTAGAGCTCC TGCGAGCTCT CTCGAGCTAG

AAGGAGCTGG GTGGAGCTAC CGTGAGCTCC CCGTAGCTCA

TGGACGCTTC CGACCGCTAG TTACCGCTCT TGCCCGCTCC

GTGCCGCTAT CGTCCGCTCT ATTCCGCTCA TTTCCGCTAG

TCGGCGCTGC TTGGCGCTTA CCATCGCTTC AGATCGCTGT

CTATCGCTGA GACTCGCTAG ACCTCGCTTA ATCTCGCTGC

CAGTCGCTAC TGTTCGCTGA AAAAGGCTGA CACAGGCTGC

GAGAGGCTGG ATGAGGCTAC TATAGGCTGT TCCCGGCTGG

AGTCGGCTTG GGAGGGCTAG AACGGGCTGT AGGGGGCTAA

TGGGGGCTCG CTGGGGCTAT GGTGGGCTCT ACTTGGCTAC

CAAATGCTTG GCCATGCTAC CCGATGCTAG GAACTGCTCC

TCACTGCTTC TTACTGCTGA TAGCTGCTAC CGTCTGCTGA

ATTCTGCTGT AGATTGCTCA TGATTGCTAG CTATTGCTCT

CGCTTGCTCC GGGTTGCTCG TGTTTGCTCT CTTTTGCTAG

CCAAATCTAC GACAATCTTG ACCAATCTAA TCCAATCTCG

CAGAATCTTC AAACATCTCA TAACATCTAG CACCATCTCC

GAGCATCTCG TCGCATCTTG TATCATCTCT GCTCATCTTT

-continued

ACAGATCTAT AAGGATCTTT ACTGATCTCG TCTGATCTAA
GGATATCTCC GTCTATCTCT TGGTATCTAC CATTATCTGA
CAAACTCTCA AACACTCTCC GGTACTCTGC ACACCTCTAC
CCCCCTCTAA AAGCCTCTTC CACGCTCTCT TATGCTCTCC
GCTGCTCTTC GTTGCTCTGA AGATCTCTTG GGGTCTCTTA
GCAAGTCTAT GAGAGTCTTT TCGAGTCTCT TATAGTCTTG
GCTAGTCTCG TGACGTCTGA GACCGTCTCT TCCCGTCTTT
CCTCGTCTTC AGTCGTCTGT CTTCGTCTGA AACGGTCTTG
GCCGGTCTAA CGATGTCTCT ATATGTCTCA TTATGTCTAG
CTCTGTCTCC GTGTGTCTCG CGTTGTCTAG TTTTGTCTCT
CAAATTCTGT AGGATTCTAC ATTCTTCTTG AAAGTTCTGC
GTAGTTCTAG CACGTTCTGA CGGGTTCTAT ATGGTTCTAA
TTGGTTCTCG GTTGTTCTCT ACCTTTCTCG TCCTTTCTAA
GTAAAAGTCT GGCAAAGTCC CGGAAAGTCG TTGAAAGTAT
AATAAAGTGC GTTAAAGTAG CGCCAAGTTG GGGCAAGTTC
TACGAAGTGC GTCGAAGTCA CATGAAGTGT GAATAAGTTG
ACATAAGTAA TCATAAGTCG CCCTAAGTAC AAGTAAGTTA
GCGTAAGTAG TCTTAAGTAT AGCACAGTTG GCGACAGTGT
TCTACAGTGG GGACCAGTCA TACCCAGTGT AGGCCAGTCG
TGGCCAGTAA CATCCAGTGC CTAGCAGTTG ACCGCAGTGG
GGGGCAGTTT TGTGCAGTTG AAATCAGTCC CACTCAGTCA
TTGTCAGTGG GTTTCAGTGT CTAAGAGTCC CGCAGAGTCT
ATCAGAGTCA TTCAGAGTAG TGTAGAGTCC GTACGAGTTG
ACGCGAGTGC CGGCGAGTTT ATGCGAGTTA CGAGGAGTCA
ATAGGAGTCT AGCGGAGTCC GATGGAGTGC ATTGGAGTAG
TTTGGAGTCA GCCTGAGTAT ACAATAGTCG TCAATAGTAA
TAGATAGTTA GCGATAGTCA ACTATAGTAT GGACTAGTGT
AACCTAGTAG TACCTAGTCA GCCCTAGTTA GTCCTAGTGC
CTGCTAGTGG TCCGTAGTAT CCTGTAGTAC CACTTAGTGT
CGGTTAGTAA ATGTTAGTAT TATTTAGTGC GTTTTAGTCA
GGCAACGTAA GAGAACGTGT TATAACGTGG TGACACGTTA
TCCCACGTGT CCTCACGTGC AGTCACGTTT CTTCACGTTA
GGAGACGTAT AACGACGTGG GTCGACGTAC TGGGACGTCT
CTGGACGTAG GGTGACGTCG ACATACGTCC CCCTACGTCA
TTAACCGTTT TGCACCGTTC ACTACCGTGC CGTACCGTTT
ATTACCGTTA GGACCCGTAC GTCCCCGTAT TGGCCCGTCC
TCCGCCGTGC TTCGCCGTTA CCTGCCGTGT AGTGCCGTTC
AAATCCGTAA TAATCCGTCG GCATCCGTTG CACTCCGTAC
GAGTCCGTAG ACGTCCGTTA ATGTCCGTGC TATTCCGTAT
AGAAGCGTAT CTAAGCGTAA GACAGCGTGG ATCAGCGTAC
CAGAGCGTGC AGTAGCGTCG TGTAGCGTAA TCGCGCGTGG

-continued

GCTCGCGTGT CGAGGCGTAC AGCGGCGTAA TGCGGCGTCG
CTCGGCGTAT AAGGGCGTGT TTTGGCGTAC CATTGCGTTA
GAAATCGTTC TCAATCGTCC CCCATCGTAG GCGATCGTAC
CAACTCGTCG TACCTCGTAC CATCTCGTAT CCTGTCGTCA
GGCTTCGTCG CGGTTCGTCC AATTTCGTGG GTTTTCGTAC
CACAAGGTCT TATAAGGTCC GCTAAGGTTC GTTAAGGTGA
CCACAGGTAT CAGCAGGTTT CCTCAGGTCG CAAGAGGTCA
AACGAGGTCC GGTGAGGTGC ACATAGGTGG CTCTAGGTTG
GCGTAGGTGA GTGTAGGTTC ACAACGGTAT AAGACGGTTT
ACTACGGTCG TCTACGGTAA AACCCGGTCT TGGCCGGTGG
GGTCCGGTGT CCAGCGGTAC GACGCGGTTG ACCGCGGTAA
TCCGCGGTCG CAGGCGGTTC TAATCGGTGC GTATCGGTCA
ATGTCGGTCG TTGTCGGTAA GACAGGGTCC TCCAGGGTTC
TTCAGGGTGA CAGAGGGTCG CCTAGGGTTT AGTAGGGTGC
GCACGGGTAC CACCGGGTTG GAGCGGGTTC TCGCGGGTCC
TTAGGGGTGT TGCGGGGTGC ACTGGGGTTC CGTGGGGTGT
ATTGGGGTGA GGATGGGTTG AGGTGGGTTA CTGTGGGTTT
TCAATGGTGG CAACTGGTGC AACCTGGTGA AGGCTGGTAT
CTGCTGGTAA GGTCTGGTCA TGAGTGGTTG CTTGTGGTTG
GTATTGGTGT GGCTTGGTGC CGGTTGGTGG AATTTGGTCC
TCGAATGTGC TTGAATGTTA GACCATGTGC ATCCATGTAG
TTCCATGTCA CAGCATGTGG AGTCATGTCC TGGGATGTTC
ACATATGTTT CGATATGTGC AGCTATGTGA CTCTATGTGT
AAGTATGTAT GATTATGTCA TCTTATGTTA TTTTATGTGC
GAAACTGTGA TTAACTGTCC TGCACTGTCT CTCACTGTAG
AAGACTGTGG GTGACTGTAC CGTACTGTCC TGGCCTGTTT
GGTCCTGTTG AGAGCTGTAG TGAGCTGTCA GACGCTGTGT
GGGGCTGTAA AGTGCTGTCT CTTGCTGTCA GCTTCTGTAC
CCTAGTGTGG CACCGTGTGT CGGCGTGTAA ATGCGTGTAT
TATCGTGTGC GTTCGTGTCA TTAGGTGTTG CGTGGTGTTG
GGATGTGTGT AACTGTGTAG TACTGTGTCA GCCTGTGTTA
GTCTGTGTGC CTGTGTGTGG GAAATTGTCT TCAATTGTTT
TGCATTGTGA TAGATTGTAT GATATTGTAG ACTATTGTTA
ATTATTGTGC GCCCTTGTAT TGAGTTGTGT GACGTTGTCA
TCCGTTGTTA TTCGTTGTGC AGTGTTGTGA CTTGTTGTGT
GTATTTGTTG ACGTTTGTGC CGGTTTGTTT ATGTTTGTTA
ACTAAATTCC TGGCAATTGC CATCAATTAA CCAGAATTAG
GACGAATTTC TCCGAATTCC CAGGAATTTG CCTGAATTCT
TAATAATTGG ATGTAATTCC TAAACATTAT GAGACATTCT
TCGACATTTT AATACATTAA TATACATTCG GCTACATTTG

```
GACCCATTTT TCCCCATTCT CCTCCATTCC AACGCATTCG
TACGCATTAA TGGGCATTGT GGTGCATTGG ACATCATTGC
CGATCATTTT ATATCATTTA CCCTCATTGA CTCTCATTTC
GTGTCATTTG TTTTCATTTT CAAAGATTTA AACAGATTTC
CCGAGATTAA TTACGATTGG AAGCGATTCC CGTCGATTGG
CACGGATTTT TATGGATTTC GCTGGATTCC AGATGATTCG
TGATGATTAA GGGTGATTCA AGTTGATTAT CTTTGATTAA
AAAATATTGG GTAATATTAC GGCATATTAT GAGATATTGA
TTGATATTCC TGACTATTTT TCCCTATTGA TTCCTATTTC
AGTCTATTTA CTTCTATTTT GGAGTATTAA AGGGTATTAG
TGGGTATTCA CCCTTATTCT GATTTATTTC TCTTTATTCC
TCAAACTTAT TAGAACTTTT GCGAACTTCT GATAACTTTG
ACTAACTTAA TCTAACTTCG GGACACTTGA TACCACTTCT
GCCCACTTTT AGGCACTTGG CATCACTTCC ACCGACTTCG
TCCGACTTAA AAATACTTGC GTATACTTAG CACTACTTGA
CGGTACTTAT ATGTACTTAA TTGTACTTCG GTTTACTTCT
GTAACCTTGT GGCACCTTGC CGGACCTTGG AATACCTTCC
CCTCCCTTAA CAAGCCTTAG TACGCCTTCC GCCGCCTTTC
GTCGCCTTGA CCGGCCTTTG CATGCCTTCT TCATCCTTGG
TACAGCTTTG GCCAGCTTCG CCGAGCTTCC GAACGCTTAG
ACACGCTTTA ATACGCTTGC CCCCGCTTTC AGCCGCTTGT
CTCCGCTTGA AAGCGCTTAA TAGCGCTTCG GCGCGCTTTG
GATCGCTTCT TCTCGCTTTT ACGGGCTTCT AATGGCTTTG
GCTGGCTTAA TGATGCTTCC CGCTGCTTAG TTCTGCTTCT
GGGTGCTTAC CTTTGCTTCC TAAATCTTCG GTAATCTTCA
ATGATCTTCG TTGATCTTAA CCACTCTTGG ATCCTCTTTG
GGAGTCTTCC GTCGTCTTCT TGGGTCTTAC CATGTCTTGA
ACATTCTTAT AAGTTCTTTT ACTTTCTTCG TCTTTCTTAA
CGAAAGTTTA ATAAAGTTTT CCCAAGTTGT AGCAAGTTTC
TCTAAGTTGC TTTAAGTTTA AGGCAGTTCC CATCAGTTGG
CCAGAGTTGA CTAGAGTTTC ACCGAGTTGC CGCGAGTTTT
ATCGAGTTTA TGTGAGTTTC AAATAGTTCG TAATAGTTAA
GAGTAGTTCA TCGTAGTTTA TTGTAGTTGC AATTAGTTAT
GGCACGTTCG CGGACGTTCC AATACGTTGG GTTACGTTAC
AGACCGTTTA CTACCGTTTT ACCCCGTTGT CGCCCGTTTC
GGGCCGTTTG TGTCCGTTTT TACGCGTTGG AGGGCGTTCT
CTGGCGTTCA GGTGCGTTAA GAATCGTTTC TCATCGTTCC
CCCTCGTTAG GCGTCGTTAC GCCAGGTTGC GTCAGGTTTA
CCGAGGTTGG ATACGGTTCG TTACGGTTAA TAGCGGTTGC
GTGCGGTTCA CGTCGGTTAA ATTCGGTTAT GTAGGGTTTT
GGCGGGTTTC CGGGGGTTTG TGATGGTTGG CTTTGGTTGG
AAAATGTTAA TAAATGTTCG GCAATGTTTG CACATGTTAC
GAGATGTTAG ACGATGTTTA ATGATGTTGC TATATGTTAT
CCACTGTTCC ACCCTGTTCA TCCCTGTTAG GGAGTGTTGG
AACGTGTTAT AGGGTGTTGA CTGGTGTTGT TTATTGTTTT
TGCTTGTTTC ACTTTGTTGC CGTTTGTTTT ATTTTGTTTA
GAAAATTTAC ATAAATTTGG CCCAATTTTG TAGAATTTCC
GCGAATTTTC GTGAATTTGA TACCATTTTC GCCCATTTCC
CCGCATTTCG CATCATTTTT CGCGATTTGG GGGGATTTGC
GCTTATTTGA GTTTATTTTC TAAACTTTTA GCAACTTTCA
ACGACTTTCG TCGACTTTAA AATACTTTTT CTACCTTTGG
GACCCTTTAA ACCCCTTTTG GGGCCTTTGT TGTCCTTTGG
TACGCTTTTT GCCGCTTTCT CATGCTTTTC CGATCTTTAA
ATATCTTTAT AGCTCTTTAC ATTTCTTTCG TTTTCTTTAA
CAAAGTTTAT CCGAGTTTTT AGGAGTTTGC CATAGTTTCG
CCCCGTTTCT GATCGTTTTC TCTCGTTTCC AAAGGTTTAC
GTAGGTTTGG CACGGTTTAA ACGGGTTTTC CGGGGTTTGT
ATGGGTTTGA TGATGTTTTT TCCTGTTTGA TTCTGTTTTC
AGTTGTTTTA CTTTGTTTTT GCAATTTTGT GGCATTTTTA
AGACTTTTCG TGACTTTTAA GGGCTTTTCA AGTCTTTTAT
CTTCTTTTAA GGAGTTTTTT GCCGTTTTGA GTCGTTTTTC
CTGGTTTTTG TTATTTTTGG AAGTTTTTCC CGTTTTTTGG
```

The foregoing code set is also applicable to the following dataset for Reed-Solomon 5+2 base, 256 sequence, 1 base error correction, 2 nocall correction:

```
AAAAAAA CCAAACA GCAAATG GGAAAGA TTAAATA AACAAGT
CACAACC ACCAAAC TCCAACG GGCAAAT CTCAATG GTCAACA
GAGAAGG AGGAAAG TGGAACC TATAATT AGTAACA ATTAAAT
AAACACC CAACAGT TAACAAG CCACAAC ATACATG CACCAAA
ACCCACA GTCCAAC CCGCATT TGGCAAA TTGCACT GATCAGC
GCTCAAT AGTCAAC TGTCACG CTTCAGA AAAGAGG TCAGACT
GGAGAAG CTAGATT GCCGATT AGCGATC GAGGAAA ACGGATG
AGGGAGA CTGGAAC CATGATA GATGACG TGTGAGC GTTGATC
AAATATT TGATACA CTATAGG TTATAAT GCCTAGG CGCTACG
GGCTATA TTCTAGA AAGTAAC TAGTACG ACGTAGT CCGTACC
GGGTAGC TTGTATC TATTAAA ATTTATA CAAACAC ACAACCC
CCAACGT TCAACAG GGAACCT GTAACAA AACACCA CCCACAA
TGCACTT GTCACGT CAGACTT ATGACGG GATACAT GCTACGC
AGTACGT CGTACCC CAACCCA GAACCTG ACACCAA GTACCCC
AACCCAC TACCCCG ACCCCGT CCCCCCC GGCCCGC TTCCCTC
GCGCCGG CGGCCCG GGGCCTA TTGCCGA TCTCCTT CGTCCAA
```

```
                         -continued
ATTCCGC CTTCCCT TCAGCGA TGAGCTG GTAGCGG TACGCGC

CCCGCGG TCCGCAT CGCGCTA GGCGCCG TAGGCTA GCGGCCC

AGGGCCT CGGGCGC ATGGCAA AATGCTC ATTGCCG TTTGCAC

CGATCAG TGATCGT GTATCTT CCCTCTT TGCTCAA TTCTCCT

CAGTCAA ACGTCCA GTGTCAC CATTCCG GATTCTA ACTTCAG

TCTTCCC CTTTCTC GAAAGAG ACAAGTA AGAAGGG AACAGTC

ATCAGCG TTCAGAC AAGAGGA GGGAGAA GTGAGCT TATAGGC

CCTAGGG TCTAGAT CGTAGTA GGTAGCG CAACGTC TCACGTG

TGACGGA CTACGCG GTACGTA CCCCGTA GCCCGCG CGCCGGG

TGCCGAT TTCCGCA CAGCGAT TAGCGGG ACGCGCT CCGCGGC

GGGCGCC GATCGTT GAAGGGA AGAGGAA ATAGGCT CTAGGGC

GACGGAT GCCGGGC AGCGGGT CGCGGCC AAGGGAG TAGGGCC

CCGGGCG GCGGGTA GGGGGGG TTGGGTG AATGGCA CCTGGAA

TGTGGTT GTTGGGT AAATGGC CAATGCT ACATGAT GGATGAC

ACCTGGA AGCTGTG ACGTGTC GGGTGTT CTGTGAG TTGTGGT

GATTGCC TCTTGTA CGTTGAT TGTTGGG CTTTGCA GTTTGTG

CAAATGG TAAATAT TCAATGC ATAATTT TACATGA CGCATTC

TAGATTC CCGATTG GCGATCA CGGATGA ATGATAC TTGATCG

AATATTA GCTATAG TGTATCT TTTATAA GCACTTT AGACTTC

AACCTGG TCCCTCT GGCCTAG CTCCTTT GAGCTGT GCGCTAC

AGGCTAT ATGCTCA TATCTTG CCTCTTC ATTCTAG TTTCTCC

CAAGTAA ACAGTCA GTAGTAC AACGTCC CACGTGT TACGTAG

CCCGTAC ATCGTTG CGGGTAG TGGGTGT GTGGTTT GCTGTGA

CGTGTCA GGTGTTG CTTGTAT TTTGTGG TAATTTA GCATTCC

AGATTCT CGATTGC ATATTAA CACTTTG GACTTCA TCCTTTC

ATCTTGT CTCTTCC TCGTTGA TGGTTTG GTGTTGG AATTTAT

ACTTTGC CCTTTCT GGTTTGT TTTTTTT
```

The error correction technique of the invention can be used in many applications. The technique will correct a base call 44 to a corrected base call 46, where the bases could part of a model system or a construct made of a tag and another sequence which could be an unknown sequence from a defined set. Once the DNA markers, for example DNA tags, are fully recovered by these methods, the population of identified bases can then be assembled to recover and correct sequence information for the target nucleic acid and/or identify the presence of particular sequences in the target nucleic acid. There is also potential for exploiting the higher accuracy of tag recovery in developing more efficient and potentially faster genome sequencing techniques, such as long fragment read (LFR) techniques. In some embodiments, the identified bases are assembled into a complete sequence through alignment of overlapping sequences obtained from multiple sequencing cycles performed on multiple DNBs. As used herein, the term "complete sequence" refers to the sequence of partial or whole genomes as well as partial or whole target nucleic acids.

Long Fragment Reads (LFR) technology enables independent sequencing and analysis of the two parental chromosomes in a diploid sample. See for example, US Published Patent Application US 2007/0072208 corresponding to PCT Published Patent Application WO2006/138284 published 28 Dec. 2006, which are incorporated herein by reference. As applied to the sequencing of polyploidy organisms, such as diploid human genomes, LFR allows heterozygote phasing over large intervals (potentially entire chromosomes), even in areas with high recombination rates. In addition, by distinguishing calls from the two chromosomes, LFR allows higher confidence calling of homozygous positions (>99% of the genome) at low coverage. Additional applications of LFR include, but are not limited to, resolution of extensive rearrangements in cancer genomes and full-length sequencing of alternatively spliced transcripts.

According to a typical application of LFR to human genomic DNA, genomic DNA of approximately 100 kbp is used as the input for LFR, as the length of input DNA impacts the interval over which phasing can be performed. This high molecular weight genomic DNA is aliquotted into a 384 well plate such that approximately 0.1 haploid genomes (10% of a haploid genome) are aliquotted into each well. The DNA fragments in each well are amplified, and this amplified DNA is fragmented to about 500 bp. The DNA in each well is ligated to adaptor aims containing a unique identifier, and the ligated DNA from all 384 wells is then pooled into a single tube.

This pooled DNA is then used as input to a standard library construction (such as that developed by Complete Genomics, Inc. of Mountain View, Calif.) and sequencing processes. In aggregate, the 384 wells will contain approximately 40 fragments, spanning each position in the genome, with about 20 fragments coming from the maternal chromosome and 20 from the paternal chromosome. At a rate of 0.1 genome equivalents per well, there is a 10% chance that fragments in a well will overlap, and a 50% chance that any such overlapping fragments are derived from separate parental chromosomes. Thus, approximately 95% of the data from a well will be derived from a single parental chromosome.

In order to resolve the parental chromosomes, the reads from each well are effectively assembled independently from other wells. The data is then mapped to one or more reference genomes, and the reads that map near each other are grouped by their unique identifiers, enabling reconstruction of the approximate 100 kbp haploid fragments in each well. Single nucleotide polymorphisms (SNPs) within the sample are then used to distinguish between 100 kbp fragments from the maternal and paternal chromosomes.

The initial 40 genome equivalents described above yield on average a 100 kbp maternal fragment starting every 5 kbp and a 100 kbp paternal fragment every 5 kbp. Thus, two consecutive maternal fragments will overlap each other on average by about 95 kbp. In the human genome, there are typically 50-150 Single Nucleotide Polymorphisms (SNPs) within 95 kbp, many of which will be heterozygous in any given sample.

Using these SNPs, maternal fragments are distinguished from paternal fragments. By chaining together overlapping fragments; large maternal and paternal segments (up to complete chromosomes) can be constructed separately. Phasing will not be possible across long repeat sections such as satellites in centromeric regions. But for most practical purposes LFR increases effective read length from 35 bp to over 100 kbp.

In further embodiments, assembly methods utilize algorithms that can be used to "piece together" overlapping sequences to provide a complete sequence. In still further embodiments, reference tables are used to assist in assembling the identified sequences into a complete sequence. A reference table may be compiled using existing sequencing data on the organism of choice. For example human genome data can be accessed through the National Center for Biotechnology Information at ftp.ncbi.nih.gov/refseq/release, or through the J. Craig Venter Institute at http://www.jcvi.org/researchhuref/. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

In any of the embodiments of the invention discussed herein, a population of nucleic acid templates and/or DNBs may comprise a number of target nucleic acids to substantially cover a whole genome or a whole target polynucleotide. As used herein, "substantially covers" means that the amount of nucleotides (i.e., target sequences) analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, *Genomics*, 2: 231-239 (1988); Vingron et al, *J. Mol. Biol.*, 235: 1-12 (1994); and like references.

Reed-Solomon (RS) code-based sensors in the form of DNB, beads and the like, may be spiked into into the mix of conventional genomic sensors on a substrate. For instance, one could construct a substrate sensor set with a mixture of 99.9% conventional genomic sensors and 0.1% RS sensors. After reading a series of bases, e.g., 10, one could select from the mix candidate RS sensors with high fidelity. The candidate RS sensors will be those that differ from the RS codes by at least K bases, where K is normally 0 or 1. These candidate RS sensors can be delivered to the RS decoding algorithm for the characterization of the system. A 0.1% spiking of RS in a lane of genomic information will provide sufficient information to enable RS analysis while providing minimal contamination to the genomic sequences, as a library would contain multiple RS codes in a DNA short-read. Other spiking densities are also contemplated, as for example as much as ten per cent but preferably in the range of one per cent to five per cent. The set that is spiked in is preferably a subset of the 4096 possible RS codes that are available. This subset is preferably optimized to have minimal hits to the genomic DNA. By doing so, no extra space needs to be set aside on the substrate for the RS sensor system. Moreover, for each lane of the genomic experiment, an internal control would be available, i.e., the RS sensors that are spiked in. Alternatively, the spiked-in RS sensors can have an independent short tag that would differentiate between them and the genomic data.

Figures 2, 3, 5:
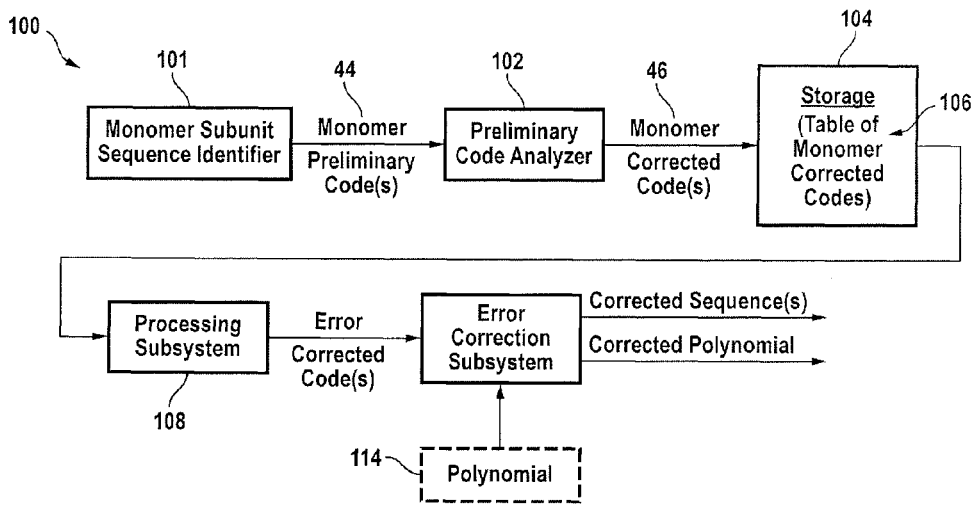
FIG. 2 is a table illustrating experimental results of the use of Reed-Solomon correction on a set of 7-mer DNA sequences.
FIG. 3 is a table summarizing a comparison of representation of a typical set of DNB calls showing improvements according to the invention
FIG. 5 is a depiction of an apparatus incorporating the invention.

FIG. 2 illustrates results of the use of Reed-Solomon correction on a set of 7-mer DNA sequences. Column 1 is an index. Column 2 is the calls of the observed sequence. Column 3 is the corrected sequence after error correction according to the invention. Column 4 indicates whether a call was recovered, i.e., changed from the observed call. Columns 5 through 11 are the scores at the seven positions for each of the bases in the seven-base sequence, i.e., the estimated likelihood that the original call was correct. The error in the scores could be a function of problems in either physical or optical interference between adjacent interrogation sites (cross-talk), a weak DNB at an interrogation site, a missing DNB at an interrogation site allowing a reading to be taken based on an adjacent interrogation site, problems in stripping, washing and flushing between sequencing cycles and errors in sequencing. In the course of processing and correction of five sequences, two bases were recovered. As a condition, the processing algorithm was blind to all scores and to all other sequences (when processing each sequence).

One of the outcomes of Reed-Solomon decoding of the genomic data is that certain sites do not result in a correction of a call. The no-call output is typically an indication that the interrogation site has more than one error, which is often the case when the interrogation site is empty and/or the report of an observed sequence is based on readings from adjacent interrogation sites (cross-talk). Thus the Reed-Solomon decoding actually identifies bad interrogation sites. FIG. 3 is a table summarizing an experiment comparing observed sequences and Reed-Solomon corrected sequences. Column 1 is the categories of A. Valid Sequences, B. Uncalled Sequences, C. Invalid Sequences, and D. Total Sequences accounted for. There was a total of 50625 7-mer sequences accounted for. Of that, 20647 were observed valid sequences and 29978 invalid sequences. After Reed-Solomon correction, the number of valid sequences increased to 35317 and 15308 sequences were designated as no-calls, eliminating all invalid sequences from the set. The result is that the Reed-Solomon correction technique was able to recover about 70% of the valid DNBs and suppress the empty interrogation sites and low-quality DNBs by designating them as no-calls.

The inventive method can operate on blocks of delimited sets of monomer subunits that are artificial DNA sequences. The artificial DNA sequences are made up of oligonucleotides, or at least one oligonucleotide. The method according to the invention works on real systems containing tags, as well as in model systems where the model content is known and used to characterize real systems. Tags may be employed in Long Fragment Read techniques. Tags are useful particularly in multiplexing a plurality of individual samples, in multiplexing a plurality of tissues of a sample, and in multiplexing multiple libraries of a sample.

In the preparation of samples wherein the monomer subunit sequence has tags, the physical elements containing the tags can be randomly placed on a substrate, the tags being used as markers to identify both location and type of subunit sequence.

It should be understood that the delimited set of monomer subunits referred to herein encompasses a sequence of nucleotides and/or a sequence of amino acids, both natural and artificial, and oligleonucleotides, both natural and artificial.

The methodology thus improves the accuracy and efficiency of DNA sequencing for a model system by increasing the true positives and true negatives, and decreasing the number of false positives and false negatives. It is also useful as a check against other sensor systems. There are numerous applications for fully-recoverable set of DNA tags. In addition to improving the accuracy of genome mapping (not applicable to genome mapping), if it were known that the DNA tags were accurate, then the other sources of error or imperfections in the analysis and preparation processes could be better identified and the errors and improvements could be quantified. Furthermore, other methods of error correction verification can be verified and calibrated. Still further, various techniques for verification and error correction can be combined to provide even higher efficiency and accuracy in the sequencing process.

FIG. 4 is a representative figure similar to FIG. 2 intended to depict 10-base codes that are a preferred embodiment.

FIG. 5 depicts a generalized apparatus 100 incorporating and operative according to another aspect of the invention. The apparatus 100 is for processing errors in data used for identifying a sequence of an oriented linear heteropolymer, such as a polynucleotide, a oligonucleotide, an amino acid and a DNA sequence, including both natural and artificial sequence types. Processing includes either identifying one or more errors in the sequence or correcting one or more errors in the sequence. The apparatus includes a subsystem 101 operative to identify the monomer subunit sequence in order to obtain preliminary codes 44, the preliminary codes intended to resemble members of an expected known delimited code set of block codes. The sequence identifier may identify as little as one preliminary code or sequence but it is preferable to identify several sequences or codes. There may be an optional analysis subsystem 102 for preliminary analysis of the preliminary codes 44 using a computer processing system, in order to obtain (analyzed) candidate codes 46. The candidate codes are stored in a table 106 in a storage subsystem 104 to expedite the processing of several sequences or codes together. The candidate codes or sequences 46 are retrieved from the storage subsystem 104 and provided to an error correction/detection, a processing subsystem 108 for detecting errors or invoking error correction. The output of subsystem 108 is an output code 114. The output code may take the form of the sequence or sequence listing that has been corrected according to the invention or a set of indicators of error content for each sequence, such as zero, one or two errors, or a no-call, indicating that the sequence is not identifiable. This system can be used for modeling, tagging, spiking of natural sequences for identification, and for error correction to correct for errors in the initial (visual) readings and, for model systems, sequence calling for a known system.

According to the invention, compositions may be formed, such as for use in modeling and improved genome sequencing, as well as other applications. Compositions may comprise linear oriented heteropolymers of blocks of monomer subunit sequence having coding of an expected known delimited code set of block codes, and specifically Reed-Solomon codes, namely codes produced according to the Reed-Solomon algorithm, and specifically those of a length between 5 and ten monomer subunits, wherein the ratio of distance between codes and length of code is at least 20 percent. Specific heteropolymer components may include polypeptides, polynucleotides, such as DNA nanoballs, oligonucleotides Such a composition may include and be attached to a substrate wherein the heteropolymers are attached at spaced apart interrogation sites, and the sites of attachment may be ordered or randomly arranged.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08407554B2). An electronic copy of the "Sequence Listing" will also be available from the USPTO upon request and payment of the fee set forth in 37 CFR 1.19(b)(3).

What is claimed is:

1. A method for processing errors in data corresponding to a sequence of an oriented linear heteropolymer comprising monomers, the method comprising:

acquiring an output of data from an apparatus operative to identify a sequence within the linear heteropolymer to obtain one or more preliminary codes, wherein a preliminary code includes a plurality of base calls, a base call being selected from a group of one of at least three possible bases and a no-call, and wherein a preliminary code is intended to resemble a member of an expected known delimited code set of block codes, and wherein at least one of the one or more preliminary codes includes at least one no-call; and for each of the preliminary codes:
applying the base calls of the preliminary code as a vector of symbols of the delimited code set; and
invoking, using a computer processing system, an error detection or correction algorithm for a block error identification on the vector to identify one or more errors in the symbols; and outputting at least one error to a storage subsystem for utilization.

2. The method according to claim 1 further including:
analyzing the preliminary codes against the expected known delimited code set, for each position of the preliminary codes associated with positions of the sequence, to obtain a candidate code set; and
assembling the candidate code set into a table of candidate codes in a storage element for said applying step.

3. The method according to claim 1 further including designating as no-calls those preliminary corrected code sequences having at least one error.

4. The method according to claim 1, wherein the block codes of the known delimited code set have a minimum distance of D+1, the method further comprising:
identifying D no-calls on a preliminary code as locations of an error; and
correcting the D no-calls using the error detection or correction algorithm.

5. The method according to claim 1, wherein a base call includes a quality score, and wherein a no-call corresponds to a base having a quality score less than a preselected confidence threshold.

6. The method according to claim 1 further including the step of generating a code set for encoding the symbols, wherein each random pair from the code set is guaranteed to have a minimum ratio R of distance D to length L of greater than 20 percent from every other member of the set.

7. The method according to claim 6 wherein the distance D is greater than or equal to 3 for length L equal to 10.

8. The method according to claim 6 wherein the distance D is greater than or equal to 3 for length L equal to 7.

9. The method according to claim 1 further including
correcting each correctable error in the preliminary codes to match with the delimited set to obtain a corrected sequence.

10. The method according to claim 9 wherein said error detection or correction algorithm is a Reed-Solomon algorithm.

11. The method according to claim 9 further including the step of generating a code set for encoding the symbols, wherein each random pair from the code set is guaranteed to have a minimum ratio R of distance D to length L of greater than 20 percent from every other member of the set.

12. The method according to claim 11 wherein the distance D is greater than or equal to 3 for length L equal to 10.

13. The method according to claim 11 wherein the distance D is greater than or equal to 3 for length L equal to 7.

14. The method according to claim 1 wherein said error detection or correction algorithm is a Reed-Solomon algorithm.

15. The method according to claim 14 wherein the block of the delimited set is an artificial DNA sequence comprising an oligonucleotide.

16. The method according to claim 14 wherein each block of the delimited set of monomer subunits includes a tag, wherein the tag is used in a Long Fragment Read technique.

17. The method according to claim 14 wherein each block of the delimited set includes a tag, further including the step of using the tag in multiplexing a plurality of individual samples.

18. The method according to claim 14 wherein each block of the delimited set includes a tag, further including the step of using the tag in multiplexing a plurality of tissues of a sample.

19. The method according to claim 14 wherein each block of the delimited set includes a tag, further including the step of using the tag in multiplexing multiple libraries of a sample.

20. The method according to claim 14 wherein the block comprises tags and wherein elements containing said tags are randomly placed on one of a patterned and unpatterned substrate.

21. The method according to claim 14 wherein the block of the delimited set is a sequence of nucleotides.

22. The method according to claim 14 wherein the sequence of bases of the nucleic acid construct is a sequence of amino acids.

23. The method according to claim 14 wherein the block of the delimited set is a sequence of amino acids.

24. The method according to claim 23 wherein the amino acids are artificial.

25. The method according to claim 23 wherein the amino acids are artificial.

26. A method for processing errors in data corresponding to a sequence of bases for each of a plurality of nucleic acid constructs, the method comprising:
acquiring a set of data representative of the nucleic acid constructs from molecular attachment sites, the set of data including labels associated with positions of the molecular attachment sites;
analyzing, using a computer processing system, the labels to obtain preliminary base calls for the sequences of the nucleic acid constructs, wherein the nucleic acid constructs comprise tags, and wherein nucleic acid constructs containing said tags are randomly placed on a substrate at the molecular attachment sites;
assembling the preliminary base calls into one or more preliminary base call sequences corresponding to a delimited set of codes for the tags;
applying the preliminary base calls of each of the preliminary base call sequences as coefficients of a polynomial;
invoking a Reed-Solomon algorithm, using a computer processing system, for detection of errors on the respective polynomials to identify one or more errors in the respective polynomials; and
outputting said identified errors to a storage device.

27. The method according to claim 26 wherein the sequence of bases of the nucleic acid construct is an artificial DNA sequence comprising an oligonucleotide.

28. The method according to claim 26 wherein each sequence of bases of the plurality of nucleic acid constructs includes a tag, wherein the tag is used in Long Fragment Read techniques.

29. The method according to claim 26 wherein each sequence of bases of the plurality of nucleic acid constructs includes a tag, further including the step of using the tag in multiplexing a plurality of individual samples.

30. The method according to claim 26 wherein each sequence of bases of the plurality of nucleic acid constructs includes a tag, further including the step of using the tag in multiplexing a plurality of tissues of a sample.

31. The method according to claim 26 wherein each sequence of bases of the plurality of nucleic acid constructs includes a tag, further including the step of using the tag in multiplexing multiple libraries of a sample.

32. The method according to claim 26 wherein the sequence of bases of the nucleic acid construct is a sequence of nucleotides.

33. The method according to claim 26 further including designating as no-calls those preliminary corrected code sequences having at least one error.

34. The method according to claim 26 wherein said outputting includes no-call sequences and no-calls within a sequence.

35. The method according to claim 26 further including correcting each single error in the preliminary base call sequences to obtain corrected base call sequences; and outputting the corrected base call sequences to a storage device.

36. The method according to claim 26, wherein the molecular attachment sites are ordered.

37. The method according to claim 26 further including the step of generating a correction code set wherein each random pair from the code set is guaranteed to have a minimum ratio R of distance D to length L of greater than 20 percent from every other member of the set.

38. The method according to claim 37 wherein the distance D is greater than or equal to 3 for length L equal to 10.

39. The method according to claim 37 wherein the distance D is greater than or equal to 3 for length L equal to 7.

40. An apparatus for processing errors in data corresponding to a monomer subunit sequence of an oriented linear heteropolymer including a nucleic acid, the apparatus comprising:

a subsystem apparatus, coupled to an apparatus operative to identify the monomer subunit sequence, for obtaining one or more preliminary codes corresponding to the monomer subunit sequence, the preliminary codes being candidates of a delimited set of codes;

a storage subsystem for assembling the candidates into a table;

an error processing subsystem for invoking, using a computer processing system, error correction or detection on the candidates to at least identify errors or for correcting each correctable error in a block of the delimited set; and an output subsystem for receiving output of said error processing system.

41. The apparatus according to claim 40 wherein said error correcting code is a Reed-Solomon code.

42. The apparatus according to claim 40 wherein the block of the delimited set is a sequence of nucleotides.

43. The apparatus according to claim 40 wherein the block of the delimited set is an artificial DNA sequence comprising an oligonucleotide.

44. The apparatus according to claim 40 wherein the block of the delimited set is a sequence of amino acids.

45. The apparatus according to claim 44 wherein the amino acids are artificial.

46. The apparatus according to claim 40, wherein the subsystem apparatus is coupled to an apparatus operative to identify a plurality of monomer subunit sequences, for obtaining one or more preliminary codes corresponding to each of the monomer subunit sequences, wherein the preliminary codes correspond to artificial sequences, and wherein the error processing subsystem is further configured for:

quantifying the identified errors; and using the quantified errors to improve identification of monomer subunit sequences of natural sequences.

47. The apparatus according to claim 46, wherein the error processing subsystem is further configured for correcting preliminary calls of a natural sequence.

48. An apparatus for correcting errors in data identifying a sequence of bases for each of a plurality of nucleic acid constructs, the apparatus comprising:

an acquisition system for acquiring a series of representations for a set of the nucleic acid constructs from molecular attachment sites;

a first data processing unit for:
analyzing, from the series of representations, labels associated with positions of the genome attachment sites to obtain preliminary base call sequences of a delimited set of codes; and
assembling the preliminary base call sequences into a table of preliminary base call sequences; and a second data processing unit for:
applying the preliminary base call sequences as coefficients in the form of a Reed-Solomon code,
invoking Reed-Solomon error correction to at least identify errors, and
correcting each single error in a block of preliminary base calls in a preliminary base call sequence to obtain a corrected base call sequence; and a data utilization system for receiving the corrected base call sequence.

49. The apparatus according to claim 48 wherein the second data processing subsystem comprises a mechanism for comparing said preliminary base call sequences against an expected set of base call sequences.

50. The apparatus according to claim 48 wherein the acquisition subsystem is an image acquisition system and wherein said representations are images.

51. The apparatus according to claim 48, wherein each preliminary base call sequence includes a tag, and wherein the second data processing unit is further configured for:
using the tags in multiplexing a plurality of samples from which non-tag parts of the plurality of nucleic acid constructs were obtained.

52. A composition comprising:
a plurality of isolated oriented linear heteropolymers, each heteropolymer comprising a preselected block of a monomer subunit sequence, the monomer subunit sequence having a coding corresponding to at least one Reed-Solomon code of a length corresponding to five to ten monomer subunits, for use in processing errors in sequencing an isolated oriented linear heteropolymer.

53. The composition according to claim 52 wherein each randomly selected pair of said heteropolymers of the set has a minimum ratio R of distance D to length L of 20 percent.

54. The composition according to claim 52 wherein the heteropolymer is a polypeptide.

55. The composition according to claim 52 wherein the heteropolymer is a polynucleotide.

56. The composition according to claim 52 wherein less than five percent of the heteropolymers comprise a preselected block of monomer subunit sequence.

57. The composition according to claim 52 wherein said heteropolymers are DNA nanoballs.

58. The composition according to claim 52 further including a substrate for attachment of a plurality of said heteropolymers.

59. The composition according to claim 58 wherein said heteropolymers are attached to said substrate at spaced apart interrogation sites.

60. The composition according to claim 52, wherein each random pair of the Reed-Solomon codes is guaranteed to have a minimum ratio R of distance D to length L of greater than 20 percent.

61. The composition according to claim 60, wherein the distance D greater than or equal to 3 for length L equal to 10.

62. The composition according to claim 60, wherein the distance D greater than or equal to 3 for length L equal to 7.

* * * * *